US011044860B2

(12) United States Patent
Tolla et al.

(10) Patent No.: US 11,044,860 B2
(45) Date of Patent: *Jun. 29, 2021

(54) METHODS AND COMPOSITIONS FOR WATERMELON WITH IMPROVED PROCESSING QUALITIES AND FIRMNESS

(71) Applicant: Seminis Vegetable Seeds, Inc., St. Louis, MO (US)

(72) Inventors: Greg Tolla, Woodland, CA (US); Benito Juarez, Davis, CA (US); Fred McCuistion, Tifton, GA (US); Joseph J. King, Davis, CA (US); Eleni Bachlava, Vallejo, CA (US); Adam M. Wentzell, Winters, CA (US); Jeffrey M. Mills, Woodland, CA (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 753 days.

This patent is subject to a terminal disclaimer.

(21) Appl. No.: 14/886,955

(22) Filed: Oct. 19, 2015

(65) Prior Publication Data

US 2016/0029584 A1 Feb. 4, 2016

Related U.S. Application Data

(60) Continuation-in-part of application No. 10/972,190, filed on Oct. 22, 2004, now Pat. No. 9,173,356, and a continuation-in-part of application No. 14/743,682, filed on Jun. 18, 2015, now Pat. No. 10,036,032, which is a division of application No. 13/600,612, filed on Aug. 31, 2012, now abandoned.

(60) Provisional application No. 60/584,964, filed on Jul. 2, 2004, provisional application No. 61/629,667, filed on Nov. 23, 2011.

(51) Int. Cl.
*A01H 6/34* (2018.01)
*A01H 5/08* (2018.01)
*A01H 1/04* (2006.01)

(52) U.S. Cl.
CPC ............. *A01H 6/342* (2018.05); *A01H 1/045* (2021.01); *A01H 5/08* (2013.01)

(58) Field of Classification Search
CPC .................................. A01H 5/08; A01H 6/342
See application file for complete search history.

(56) References Cited

U.S. PATENT DOCUMENTS

| | | |
|---|---|---|
| 5,866,764 A | 2/1999 | Gabor et al. |
| 6,096,944 A | 8/2000 | Vierling et al. |
| 6,207,367 B1 | 3/2001 | Helentjaris et al. |
| 6,399,855 B1 | 6/2002 | Beavis |
| 6,414,226 B1 | 7/2002 | Hoogstraten |
| 6,639,132 B1 | 10/2003 | Duvick et al. |
| 6,670,530 B2 | 12/2003 | Eby et al. |
| 9,173,356 B2 * | 11/2015 | Tolla .................. A01H 1/00 |
| 9,420,753 B2 * | 8/2016 | Tolla .................. A01H 1/02 |
| 2003/0172412 A1 | 9/2003 | Zhang et al. |
| 2005/0015827 A1 | 1/2005 | Podlich et al. |
| 2005/0204780 A1 | 9/2005 | Moridaira et al. |
| 2005/0216545 A1 | 9/2005 | Aldrich et al. |
| 2005/0218305 A1 | 10/2005 | Tsukamoto et al. |
| 2006/0005284 A1 | 1/2006 | Tolla et al. |
| 2009/0031438 A1 | 1/2009 | Kennard et al. |
| 2010/0306883 A1 | 12/2010 | Tolla et al. |

FOREIGN PATENT DOCUMENTS

| | | |
|---|---|---|
| WO | 03/051103 A2 | 6/2003 |
| WO | 03/096798 A1 | 11/2003 |

OTHER PUBLICATIONS

Mauricio, Rodney. "Mapping quantitative trait loci in plants: uses and caveats for evolutionary biology." Nature Reviews Genetics 2.5 (2001): 370-381. (Year: 2001).*
Mauricio, Rodney. "Mapping quantitative trait loci in plants: uses and caveats for evolutionary biology." Nature Reviews Genetics 2.5 (2001): 370-381. (Year: 2001).*
Sandlin (Genetic Mapping in Citrullus lanatus, Thesis,University of Georgia, Dec. 2010 (Year: 2010).*
Accession No. PI296341 retrieved from USDA on Aug. 28, 2014, ARS, National Genetic Resources Program. *Germplasm Resources Information Network—(GRIN)*. [Online Database] National Germplasm Resources Laboratory, Beltsville, Maryland. available at http://www.ars-grin.gov/cgi-bin/npgs/acc/display.pl?1224324, in parent U.S. Appl. No. 10/972,190.
Bang et al., *Journal of Horticultural Science*, 76(6):885-890 (2004), in parent U.S. Appl. No. 10/972,190.
Buttrose et al., *Ann. Bot.*, 42:599-608 (1978), in parent U.S. Appl. No. 10/972,190.
Cartaxo et al., "Controlled Atmosphere Storage Suppresses Microbial Growth on Fresh-Cut Watermelon, "*Proc. Fla. State Hort. Soc.*, 110:252-257 (1997), in parent U.S. Appl. No. 10/972,190.
Crall et al., *Soil and Crop Set Soc.. Fla.*, Proc 4:132-134 (1986), in parent U.S. Appl. No. 10/972,190.
Crall, "'Charlee' Watermelon," *HortScience*, 25(7):812-13 (1990), in parent U.S. Appl. No. 10/972,190.
Extended European Search Report, dated Sep. 14, 2009, in EP 05764293.6, in parent U.S. Appl. No. 10/972,190.

(Continued)

*Primary Examiner* — Lee A Visone
(74) *Attorney, Agent, or Firm* — Arnold & Porter Kaye Scholer LLP; Alissa M. Eagle; David R. Marsh

(57) ABSTRACT

A watermelon plant that produces fruit having (i) ultra-firm flesh and/or liquid-retaining flesh and (ii) soluble solids of at least about 6 brix. The invention further provides for unique watermelon plants with an ultra-firm flesh phenotype and their progeny. Such plants may comprise an introgressed QTL associated with an ultra-firm flesh phenotype. In certain aspects, compositions, including distinct polymorphic molecular markers, and methods for producing, breeding, identifying, selecting, and the like of plants or germplasm with an ultra-firm flesh phenotype are provided.

34 Claims, 6 Drawing Sheets

Specification includes a Sequence Listing.

(56) References Cited

OTHER PUBLICATIONS

Extended European Search Report dated Jun. 15, 2012, in European Patent Application No. 12151233.9 in parent U.S. Appl. No. 10/972,190.
Fonseca et al., "Shock and Vibration Forces Influence the Quality of Fresh-Cut Watermelon," *Proc. Fla. State Hort. Soc.*, 112:147-152 (1999), in parent U.S. Appl. No. 10/972,190.
Gilreath et al., "Evaluation of Icebox Watermelon Cultivars in West Central and Southwest Florida," *Proc. Fla. State Hort. Soc.*, 99:331-334 (1986) in parent U.S. Appl. No. 10/972,190.
Grin Library Accession Pi 635683, publically available 1963, in parent U.S. Appl. No. 10/972,190.
Grin Library Accession Grif 15895, publically available 2003, in parent U.S. Appl. No. 10/972,190.
Hawkins et al., "Linkage Mapping in a Watermelon Population Segregating for Fusarium Wilt Resistance," *Journal of the American Society for Horticultural Science*, 126(3):344-50 (2001), in parent U.S. Appl. No. 13/600,612.
Jaskani et al., "Comparative Study on Vegetative, Reproductive and Qualitative Traits of Seven Diploid and Tetraploid Watermelon Lines," *Euphytica*, 145:259-268 (2005), in parent U.S. Appl. No. 10/972,190.
Jeffreys Seed Company Online, "Hybrid Watermelon" (4 pages printed on Mar. 30, 2004), in parent U.S. Appl. No. 10/972,190.
Kano, *J. Hort. Sci. Biotechnol.*, 79 :142-145 (2004), in parent U.S. Appl. No. 10/972,190.
Karakurt et al., "Cell Wall-Degrading Enzymes and Pectin Solubility and Depolymerization in Immature and Ripe Watermelon (*Citrullus ianatus*) Fruit in Response to Exogenous Ethylene," *Physiologia Plantarum*, 116(3):398-405 (2002), in parent U.S. Appl. No. 10/972,190.
Karchi et al., Hassadeh 61:1284-1285 (1981), in parent U.S. Appl. No. 10/972,190.
Karchi et al.,"'Alena' Watermelon," *HortScience*, 16(4):573 (1981), in parent U.S. Appl. No. 10/972,190.
Karchi et al., "The Importance of Cultural Practices in Materializing Yield Potential in a Tetraploid Watermelon Cultivar," *Cucurbit Genetics Cooperative Report*, 6:59-61 (article 30) (1983), in parent U.S. Appl. No. 10/972,190.
Leskovar et al., "Deficit Irrigation Influences Yield and Lycopene Content of Diploid and Triploid Watermelon," *Vegetable Production & Marketing News* (Mar. 2002), ed. Frank J. Dainello (Extension Horticulture, Texas Cooperative Extension, the Texas A&M University System, College Station, TX), in parent U.S. Appl. No. 10/972,190.
Leskovar et al., *Acta Hort.* 628 :147-151 (2003), in parent U.S. Appl. No. 10/972,190.
Leskovar et al., "Lycopene, Carboyhdrates, Ascorbic Acid and Yield Components of Diploid and Triploid Watermelon Cultivars are Affected by Deficit Irrigation," *J. Hort. Sci. & Biotech.*, 79(1):75-81 (2004), in parent U.S. Appl. No. 10/972,190.
Levi et al., "A Genetic Linkage Map for Watermelon Based on Randomly Amplified Polymorphic DNA Markers," *J. Amer. Soc. Hort. Sci.*, 126(6):730-737 (2001), in parent U.S. Appl. No. 10/972,190.
Li et al., "Selection and cultivation of the high quality early ripe variety Nongfong No. 1 B," *Chinese J. Selection and Cultivation of Variety*, 3:11-13 (2004) (with English translation), in parent U.S. Appl. No. 10/972,190.
Mao et al., "Incidence of water-soaking and phospholipid catabolism in ripe watermelon (*Citrullus lanatus*) fruit: induction by ethylene and prophylactic effects of 1-methylcyclopropene," *Postharvest Biology and Technology*, 33:1-9 (2004), in parent U.S. Appl. No. 10/972,190.

Martyn et al., "Resistance to Races 0, 1 and 2 of Fusarium Wilt of Watermelon in *Citrullus* sp. PI-296341-FR," *HortScience*, 26(4):429-432 (1991), in parent U.S. Appl. No. 10/972,190.
Maynard et al., "Triploid Watermelon Cultigen Evaluation," Gulf Coast Research and Education Center, GCREC Research Report BRA-2003 (Spring 2003), in parent U.S. Appl. No. 10/972,190.
Nerson et al., *Hassadeh*, 62 :606-607 (1982), in parent U.S. Appl. No. 10/972,190.
Netzer et al., "PI 296341, A Source of Resistance in Watermelon to Race 2 of *Fusarium Oxysporum f.* sp. *Niveum,*" *Plant Disease*, 73(6):518 (1989), in parent U.S. Appl. No. 10/972,190.
Nip et al., "Physical, Chemical and Organoleptic Attributes of 'Charleston Gray' Watermelons at Different Stages of Maturity," *Proc. Amer. Soc. Hort. Sci.*, 93:547-551 (1968), in parent U.S. Appl. No. 10/972,190.
Perkins-Veazie et al., "Shelf Life of Minimally Processed Watermelon," *HortScience*, 33(4):605 (1988), in parent U.S. Appl. No. 10/972,190.
Perkins-Veazie et al., "Flesh quality and lycopene stability of fresh-cut watermelon," *Postharvest Biology and Technology*, 31:159-166 (2004), in parent U.S. Appl. No. 10/972,190.
Picha, "Storage temperature influences watermelon quality," *Louisiana Agriculture*, 31(2):4-5 (1998), in parent U.S. Appl. No. 10/972,190.
Risse et al., "Sensitivity of Watermelons to Ethylene During Storage," *HortScience*, 17(6):946-948 (1982), in parent U.S. Appl. No. 10/972,190.
Risse et al., "Storage Characteristics of Small Watermelon Cultivars", *Journal of the American Society for Horticultural Science*, 115(3) 440-443 (1990), in parent U.S. Appl. No. 10/972,190.
Sandlin, "Genetic Mapping in *Citrullus lanatus*," Thesis, University of Georgia, pp. 1-84 (2010), in parent U.S. Appl. No. 13/600,612.
Showalter, "Deformation and Breakage Properties of Watermelon Flesh," *Proc. Fla. State Hort. Soc.*, 81:235-239 (1968), in parent U.S. Appl. No. 10/972,190.
Slater et al., "Plant Biotechnology: the genetic manipulation of plants 39," Oxford University Press, 2:37-53 (2003), in parent U.S. Appl. No. 10/972,190.
Smith, "Embryo Culture of a Tomato Species Hybrid," *Proc. Am. Soc. Hort. Sci*, 44:413-416 (1944), in parent U.S. Appl. No. 10/972,190.
Strang et al., "Triploid Mini-Watermelon Variety Trial" (Department of Horticulture, University of Kentucky, Lexington, KY) (2004), in parent U.S. Appl. No. 10/972,190.
US Seedless Press (Citrus and Vegetable Magazine, Feb., 1999), in parent U.S. Appl. No. 10/972,190.
US Seedless Orange Varieties (<http://www.usseedless.com/orange_varieties.htm>), retrieved from internet Oct. 1, 2014, in parent U.S. Appl. No. 10/972,190.
Wehner et al., "Breeding and Seed Production," *ASHS Horticulture Crop Production Series*, Chapter 3:27-73 (2001), in parent U.S. Appl. No. 10/972,190.
Wehner et al., "Watermelons : Charateristics, Production and Marketing," *American Society for Horticultural Science*, Alexandria, VA (2001), in parent U.S. Appl. No. 13/600,612.
Yamasaki et al., "Mineral Concentrations and Cytokinin Activity in the Xylem Exudate of Grafted Watermelons as Affected by Rootstocks and Crop Load," *J. Japan. Soc. Hort. Sci.*, 62(4):817-826 (1994), in parent U.S. Appl. No. 10/972,190.
Zhumei et al., "Selection and cultivation fo the high quality early ride variety Nongfong No. 1B," *Pingzhong Shuanyu* 3:11-13 (2004), in parent U.S. Appl. No. 13/600,612.

* cited by examiner

SEQUENCE LISTING

```
<160> NUMBER OF SEQ ID NOS: 18

<210> SEQ ID NO 1
<211> LENGTH: 120
<212> TYPE: DNA
<213> ORGANISM: Citrullus lanatus
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: allele
<222> LOCATION: (61)..(61)
<223> OTHER INFORMATION: r = g or a or deletion

<400> SEQUENCE: 1
gacaactgca agagaantttt ttcaacatga aacattcttc agcaaggaat gttatcgagc      60
ragcgtttgg gttgctaaag cagcagtggg ctattcttag tgaaacataa ttctatccaa     120

<210> SEQ ID NO 2
<211> LENGTH: 121
<212> TYPE: DNA
<213> ORGANISM: Citrullus lanatus
<220> FEATURE:
<221> NAME/KEY: allele
<222> LOCATION: (61)..(61)
<223> OTHER INFORMATION: w = a or t/u

<400> SEQUENCE: 2
```

```
ttgaaagtta ttcgtttact gaatgatgag gcgattggca tatcaaaagt ctcctttatt    60
wgacgaggct aagagttgtg gatatgatct ggaagttgtc tctttctctc atattcgtta   120
t                                                                  121

<210> SEQ ID NO 3
<211> LENGTH: 121
<212> TYPE: DNA
<213> ORGANISM: Citrullus lanatus
<220> FEATURE:
<221> NAME/KEY: allele
<222> LOCATION: (61)..(61)
<223> OTHER INFORMATION: r = g or a

<400> SEQUENCE: 3
ggtggaacta agctcgacaa caatgagcat caacctaccg agcgagaagg cactattgcg    60
rttagcaaca tggaaaagta gtcctgatct tcgttctcgt gtagactatg tcttaggact   120
t                                                                  121

<210> SEQ ID NO 4
<211> LENGTH: 121
<212> TYPE: DNA
<213> ORGANISM: Citrullus lanatus
<220> FEATURE:
<221> NAME/KEY: allele
<222> LOCATION: (61)..(61)
<223> OTHER INFORMATION: r = g or a
<220> FEATURE:
<221> NAME/KEY: misc_feature
<222> LOCATION: (77)..(77)
<223> OTHER INFORMATION: n is a, c, g, or t

<400> SEQUENCE: 4
ggactccagc cagaacatag acatccccca cccccatctg aaaaactaat attgtcccca    60
rtgtgagaaa agaaaanaag agcatgggac aaatgagaag ggaaacaaag aacttccctg   120
a                                                                  121

<210> SEQ ID NO 5
<211> LENGTH: 121
<212> TYPE: DNA
<213> ORGANISM: Citrullus lanatus
<220> FEATURE:
<221> NAME/KEY: allele
<222> LOCATION: (61)..(61)
<223> OTHER INFORMATION: m = a or c

<400> SEQUENCE: 5
tcaacaataa ccctagagaa gaccttaaca aacacttgaa ggattttcac atctgaggac    60
mtttccattc tctttgaagg atggacaaat gattggttgt actatcaacc tcctggatcg   120
a                                                                  121

<210> SEQ ID NO 6
<211> LENGTH: 105
<212> TYPE: DNA
<213> ORGANISM: Citrullus lanatus
<220> FEATURE:
<221> NAME/KEY: allele
<222> LOCATION: (45)..(45)
<223> OTHER INFORMATION: m = a or c or deletion

<400> SEQUENCE: 6
tgcaggtatc cttatgatct gaaatatcat caagattaca cttamtcgct tgaataatca    60
gaaatttcaa agtgttttat tacctgtaat cttcaaaaag aagca                  105
```

<210> SEQ ID NO 7
<211> LENGTH: 121
<212> TYPE: DNA
<213> ORGANISM: Citrullus lanatus
<220> FEATURE:
<221> NAME/KEY: allele
<222> LOCATION: (61)..(61)
<223> OTHER INFORMATION: y = t/u or c or deletion

<400> SEQUENCE: 7

```
aggataaaca aattcacata cacttttccc aaatacattt aaaaggaaaa ttggagaggg    60
ycaaataagt caagaggcta agctgtaatg aatataacag ctttgttcaa gttaaaccaa   120
t                                                                  121
```

<210> SEQ ID NO 8
<211> LENGTH: 120
<212> TYPE: DNA
<213> ORGANISM: Citrullus lanatus
<220> FEATURE:
<221> NAME/KEY: allele
<222> LOCATION: (61)..(61)
<223> OTHER INFORMATION: y = t/u or c or deletion

<400> SEQUENCE: 8

```
acaaaattct ttccaaaaat gtaaaattct caattatgga agttggcgc cgcgatgcta    60
ytggctagag ccgcggtgct gtgcgtcatg caaacctacc ctcggcgctg tgccgcagcg   120
```

<210> SEQ ID NO 9
<211> LENGTH: 121
<212> TYPE: DNA
<213> ORGANISM: Citrullus lanatus
<220> FEATURE:
<221> NAME/KEY: allele
<222> LOCATION: (61)..(61)
<223> OTHER INFORMATION: m = a or c or deletion

<400> SEQUENCE: 9

```
gaaatttagg ccacccacat gccttcttcg agtccttcag cattgggggt tatctttgta    60
mtcgagttac ccacatgcct tgtccgagtc cttcaacatt gggaaccatt tctatatctc   120
g                                                                  121
```

<210> SEQ ID NO 10
<211> LENGTH: 120
<212> TYPE: DNA
<213> ORGANISM: Citrullus lanatus
<220> FEATURE:
<221> NAME/KEY: allele
<222> LOCATION: (61)..(61)
<223> OTHER INFORMATION: y = t/u or c

<400> SEQUENCE: 10

```
cttctcggaa atacttcatc tctatggaca tcaccttcct tgaggataaa cccttctttc    60
ycgttagtcc tcgtcaggga gagagtagta gtgaagagac taactgttca tcaccttcaa   120
```

<210> SEQ ID NO 11
<211> LENGTH: 121
<212> TYPE: DNA
<213> ORGANISM: Citrullus lanatus
<220> FEATURE:
<221> NAME/KEY: allele
<222> LOCATION: (61)..(61)
<223> OTHER INFORMATION: r = g or a
<220> FEATURE:

```
<221> NAME/KEY: misc_feature
<222> LOCATION: (108)..(108)
<223> OTHER INFORMATION: n is a, c, g, or t

<400> SEQUENCE: 11
ggtcacagat tcaatctcta aagttgtatg ccaccaaact tagaacctgc aattactacg    60
ratttgacat ccatatacca caaatgaatc tacacgtttg ttgttttnaa tgaactaaaa   120
a                                                                   121

<210> SEQ ID NO 12
<211> LENGTH: 120
<212> TYPE: DNA
<213> ORGANISM: Citrullus lanatus
<220> FEATURE:
<221> NAME/KEY: allele
<222> LOCATION: (61)..(61)
<223> OTHER INFORMATION: y = t/u or c

<400> SEQUENCE: 12
atattcgagt tggccaaata ggtaacttat tattttcttg agtttgttaa catgataata    60
ytactcaacg aaatcctatg atagctacac atttgagaat gcataaacaa actcgtattg   120

<210> SEQ ID NO 13
<211> LENGTH: 99
<212> TYPE: DNA
<213> ORGANISM: Citrullus lanatus
<220> FEATURE:
<221> NAME/KEY: allele
<222> LOCATION: (61)..(61)
<223> OTHER INFORMATION: k = g or t/u

<400> SEQUENCE: 13
aaaattttat gtacaggctg ttacagttcg tcctttatct gctgtcagct ccctcgtacg    60
ktttgcagag gagccccaga tgtttgccat tgaattact                           99

<210> SEQ ID NO 14
<211> LENGTH: 120
<212> TYPE: DNA
<213> ORGANISM: Citrullus lanatus
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: allele
<222> LOCATION: (61)..(61)
<223> OTHER INFORMATION: w = a or t/u
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t

<400> SEQUENCE: 14
gtttggaact gttatatccc cntaaactgc tcaatgttat ctcagagtga gcttctacca    60
wtaaagctcc ttgttctggt nccaaaaaac acttccacct tccnatttt nggtctctct   120

<210> SEQ ID NO 15
<211> LENGTH: 120
```

```
<212> TYPE: DNA
<213> ORGANISM: Citrullus lanatus
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: allele
<222> LOCATION: (61)..(61)
<223> OTHER INFORMATION: y = t/u or c
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t

<400> SEQUENCE: 15
caattgctgc agatgtaact gaaagaacaa tcaangttct aggatggcat cattttgagt      60
ytagtttcct aataaagtgt tcatctgtgt tttngatgtg ctaaatcagt ggaggcnttt     120

<210> SEQ ID NO 16
<211> LENGTH: 121
<212> TYPE: DNA
<213> ORGANISM: Citrullus lanatus
<220> FEATURE:
<221> NAME/KEY: allele
<222> LOCATION: (61)..(61)
<223> OTHER INFORMATION: y = t/u or c

<400> SEQUENCE: 16
tgacggcggt tgctgcattg ctcatggctg tatggttcat gtctacgatt ggatgctcga      60
ygaacaccct ccgatcaatc tcgattatca gcgagtcaac gatgttgggt ggatcgatgc     120
t                                                                    121

<210> SEQ ID NO 17
<211> LENGTH: 121
<212> TYPE: DNA
<213> ORGANISM: Citrullus lanatus
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: allele
<222> LOCATION: (61)..(61)
<223> OTHER INFORMATION: r = g or a

<400> SEQUENCE: 17
acttaattga atctaataga tgaagttcaa ttacgcaagt acaaaaantt actagttaat      60
rtgtcataca cgcaagtcaa agatctttat gcatggtgcc tccaatttgt tatcagagac     120
c                                                                    121

<210> SEQ ID NO 18
<211> LENGTH: 121
<212> TYPE: DNA
<213> ORGANISM: Citrullus lanatus
<220> FEATURE:
<221> NAME/KEY: allele
<222> LOCATION: (61)..(61)
<223> OTHER INFORMATION: y = t/u or c
```

```
<400> SEQUENCE: 18
gtatcttttg tgtccgtatt agcttgcgac ctcttcgagt ggttatagtt aggttgtacg      60
ytttgatgtt tttctatgtt ggtatgagtg gcttggggat tcttttcgga gcattcatgt     120
t                                                                     121
```

METHODS AND COMPOSITIONS FOR WATERMELON WITH IMPROVED PROCESSING QUALITIES AND FIRMNESS

CROSS-REFERENCE TO RELATED APPLICATIONS

This application is a continuation-in-part of U.S. application Ser. No. 10/972,190 filed Oct. 22, 2004 (allowed Jun. 19, 2015), which claims the benefit of U.S. Provisional Patent Application No. 60/584,964 filed Jul. 2, 2004; this application is also a continuation-in-part of U.S. application Ser. No. 14/743,682 filed Jun. 18, 2015, which is a divisional of U.S. application Ser. No. 13/600,612 filed Aug. 31, 2012, which claims priority to U.S. Provisional Patent Application No. 61/529,667 filed Aug. 31, 2011, each of which are hereby incorporated by reference in their entireties.

INCORPORATION OF SEQUENCE LISTING

A sequence listing contained in the file named "P34326US00_ST25.txt" which is 7,527 bytes (measured in MS-Windows) and comprising 18 nucleotide sequences, created on Oct. 19, 2015, is electronically filed herewith and is incorporated herein by reference in its entirety.

FIELD OF THE INVENTION

The field of the present invention is watermelon breeding and the genetic improvement of watermelon. More specifically, this application is related to diploid, tetraploid and triploid watermelon seeds and plants for the production of watermelon fruit that (i) have ultra firm flesh and/or liquid-retaining flesh and (ii) are sweet at maturity. The application further relates to methods for producing, breeding, identifying, selecting, and the like of such plants or germplasm are provided.

BACKGROUND OF THE INVENTION

Watermelon (*Citrullus lanatus*) is an important commercial member of the Cucurbitaceae family that includes many different varieties. The fruits The fruit of these varieties differ in coloring, sweetness, and other traits. For example, watermelon fruit of different varieties display a wide range of coloring on the outside rind. In addition, color in the edible tissue varies from different shades of red to orange to yellow to white. Additional variation in the marketplace can be found with both seeded and seedless types. Watermelon fruit also vary in sweetness, which can be estimated by measuring total soluble solids, or brix, using a refractometer. Because sweetness is especially important to consumers, the U.S. Department of Agriculture has set fruit quality standards based on brix levels (United States Standards for Grades of Watermelon, U. S. Department of Agriculture (1978)). According to these standards, edible parts of the fruit having not less than 8 brix are deemed to be "Good", while edible parts of the fruit having not less than 10 brix are deemed to be "Very Good."

Consumers also have the choice of either seeded or seedless watermelon varieties. Unlike the flesh coloring, which is caused by varying genetic loci, the distinction between seeded and seedless varieties is usually caused by human intervention of making crosses that vary ploidy levels. Similar to humans, watermelons are natural diploids with chromosomes arranged in pairs. Many plants, including watermelons, can undergo a duplication of their entire set of chromosomes and exist as tetraploids. While it is uncommon for watermelons to produce spontaneous tetraploids, this process can be routinely produced in the laboratory using cell biology techniques. A tetraploid parent may then be crossed with a diploid parent to produce triploid seeds, which, in turn, generate plants with seedless fruits. In particular, seed formation in the fruit of triploid plants aborts because of the ploidy level differences, resulting in seedless fruits. Many commercial varieties are triploid and seedless.

Fruits of plants of different ploidy also vary in flesh firmness. Diploid lines typically have the lowest fruit flesh firmness levels. For reasons that are unclear, the process of changing a diploid line to a tetraploid line correlates with firmer fruit flesh. In other words, tetraploid lines usually have firmer fruit flesh than diploids. Triploids, being a cross between a tetraploid and a diploid, typically have an intermediate level of fruit flesh firmness.

In addition to consumer preferences as to coloring, sweetness and seeds, there is increasing consumer demand in the fresh produce business for products that combine quality and convenience. Examples of products that meet these criteria include bagged mini-baby carrots, broccoli and cauliflower and bagged leafy crops, such as lettuce and spinach. Similarly, there is a demand for mature cut fruits, like watermelon, melon, mango, pineapple, *papaya*, and kiwi. A growing segment of watermelon retail sales are cut fruits that are either displayed in large pieces with the rinds attached, or are cut into smaller pieces, without the rind, and offered to the consumers in plastic food containers. The industry term for these products is "minimally processed." By 1998, Perkins-Veazie et al. ((1998) *Hortscience* 33:605) estimated that 10% of the retail watermelon market was minimally processed.

The advantage of such cut fruit displays is that the consumer can visually inspect the quality of the fruit, and, in particular, judge whether the fruit is mature and, thus, ready to consume. Often, immature fruits will not be uniform in pigmentation, and overripe fruit will display signs of decay. Moreover, these products offer convenience to the consumer.

The disadvantage to the produce retailer in presenting minimally processed watermelon products is that cut fruits have a short shelf life. Studies indicate that minimally processed products have a short shelf life of about 2 to 3 days maximum (Wehner et al., In: Watermelons: Characteristics, Production and Marketing. Maynard, editor. ASHS Press, Alexandria Va. 2001.).

Watermelon fruits currently available typically undergo rapid quality deterioration after being cut. Cutting the fruit causes decay, which is observed as a softening of the fruit texture. Deterioration is also manifested as liquid leakage; in some varieties, the flesh of a fresh cut watermelon fruit quickly becomes unattractive to the consumer. The rapid deterioration of cut watermelon fruit places both time and space constraints on the retailer. Because cut fruits have a short shelf life, the retailer typically performs the processing on the retail site. In addition, the retailer has to monitor the products often to ensure that deteriorating products are discarded.

Unlike the sweetness standards established by the U.S. Department of Agriculture, there are no industry standards to describe the firmness of the edible portions of watermelon fruits. Therefore, there are a wide range of descriptors in use, from "firm" and "crisp" (Erma Zaden catalog descriptors for varieties Gil 104 and Erma 12) to "very firm flesh" (Zhang et al.), in U.S. Patent Publication Nos: 2004/0060085 and 2003/0217394 and in a *Seminis* watermelon catalog for the variety Cooperstown. *Seminis* has described cultivars Fenway, Royal Star, and Sentinel as having "excellent crispness", "firm flesh", and "crisp juicy flesh", respectively. In addition, Rogers Seed Company advertises the Tri-X Brand 626 as "exceptionally firm" and the Tri-X Brand 313 as having "firm texture" and "crispness of flesh".

While advertising terminology used to describe watermelon fruit flesh firmness is quite variable, scientific reports, using quantitative measurements, show that typical commercial germplasm have had substantially lower flesh firmness than the watermelon fruit of this invention. For example, Roberts et al. (2004 Report from: Watermelon Research and Development Working Group. 24th Annual Meeting, Tulsa, Okla.) measured flesh firmness in a wide range of germplasm, using a penetrometer to measure the amount of force resisted. The data were reported in Newtons, an International System of Measurements term. For purposes of comparison with Applicants' penetrometer measurements, Applicants converted Roberts' data to pounds force (lbf), using the following formula: 1 lbf=4.448 Newtons. Roberts reports a range of watermelon flesh firmness between approximately 1.4 to 3.4 lbf. One of the lines analyzed is Rogers Seed Company line Tri-X Brand 313. As noted above, Rogers Seed Company advertises this line as having "firm" flesh. Roberts et al. measured the flesh firmness in Tri-X Brand 313 as 10.84 Newtons, which converts to approximately 2.4 lbf. Applicants also tested the flesh firmness of Tri-X Brand 313, using a penetrometer from QA Supplies in Norfolk, Va. (Model FT011) with a probe diameter of 8 mm. Using this methodology, Tri-X Brand 313 has a flesh firmness reading of 1.4 lbf (Table 1). Because Roberts does not report the size of the penetrometer probe used, Applicants cannot directly compare their data to Roberts'. At least for Tri-X Brand 313, the approximately 77% higher reading measured by Roberts et al. compared with the protocol described herein may be the result of different methodology, and, in particular, the use of differently sized penetrometer probes. Although the Applicants of this invention use an 8 mm probe, another commonly used penetrometer has a diameter of 11 mm, which would account for the different readings, as penetrometer area is approximately 73% higher for an 11 mm probe as compared to an 8 mm probe.

Schultheis and Thompson (2004 Report from: Watermelon Research and Development Working Group. 24$^{th}$ Annual Meeting, Tulsa, Okla.) also survey watermelon fruit flesh firmness. Although these authors use a different model penetrometer than that used by Applicants, they use a very similarly sized probe with a diameter of 5/16" or about 8 mm. Schultheis and Thompson report that line Tri-X 313 had flesh firmness readings between 1.4 and 1.7, which are similar to Applicants' measurements, shown in Table 1. In this report, however, the authors describe these firmness data in units of pounds/square inch. It is suspected, however, that the units provided in the Schultheis and Thompson report should be in pounds force, as a reading of 1.4 pounds/square inch, using a 5/16" probe, is only 0.15 pounds force.

Maynard and Sidoti (2003 GCREC Research Report BRA-2003; Univ. Florida, Gulf Coast Research and Education Center, Bradenton, Fla.) report an additional survey of fruit flesh firmness of commercial watermelon lines. In this study, the authors use a different model penetrometer than that Applicants use in the method described herein, with a larger sized probe having a diameter of 7/16" or about 11 mm. Their firmness data range from 1.8 to 3.0 pounds/square inch. As with the Schultheis and Thompson report, Applicants believe that these authors are using the incorrect units in their firmness readings. Assuming that these data are actually in pound force units, they compare well with the results obtained using the methodology described herein. For example, Maynard and Sidoti's firmness measurement of line Tri-X 313 was 2.6. If one adjusts this figure to correct for the approximate 2 times difference in probe area, the new figure is 1.35, which is nearly identical to Applicants' measurement of this same line, (Table 1). On the other hand, if one assumes that the data are correctly reported in lb/square inch, the figure of 2.6 lb/square inch based on a 7/16" probe would be reading of 0.39 lbf. The Tri-X 313 line should have a much higher firmness reading than 0.39 lbf, providing further evidence of inconsistency in how such units have been reported in the prior art.

Leskovar et al. ((2004) *J. Horticultural Science and Biotechnology* 79: 75-81) also report watermelon fruit firmness. Although this manuscript uses a different measurement protocol, the authors describe in detail their methods, allowing the data to be converted for comparison with the data described herein. After converting to the same units, the range of germplasm analyzed had fruit firmness between 0.9 lbf and 1.5 lbf.

Although measurements of the prior art can be confusing, there is clarity that commercial watermelon lines produced prior to this invention have fruit firmness that is well below 3 lbf. In addition, as shown in Example 5, the fruit of such commercial watermelon lines, once cut, undergo significant liquid leakage. The present invention, therefore, addresses the need in the marketplace for watermelon lines that produce fruits that have a longer shelf life when processed. Specifically, the watermelon of this invention have (i) ultra firm flesh, which avoids the problem of cut fruit becoming overly soft, and/or (ii) liquid-retaining flesh, which delays deterioration of cut fruit by liquid leakage. In addition, these fruits have quality characteristics desired by the consumer, such as sweetness and attractiveness, and offer the retailer both flexibility as to where fruit processing occurs and additional shelf life once fruit is processed.

SUMMARY OF THE INVENTION

This invention relates to unique watermelon inbred lines and hybrid varieties that produce fruit having ultra firm edible flesh at maturity that resists at least 3.0 Pounds force (lbf) (measurement techniques defined herein). In addition to the novel ultra firm flesh phenotype, these fruits meet market requirements for sweetness, having not less than 6 brix for the edible tissue (measurement techniques defined herein).

Watermelons of this invention are preferably diploid and tetraploid inbred lines that produce sweet tasting ultra firm flesh at maturity that resists at least 3.5 lbf, though lines that produce sweet tasting ultra firm flesh at maturity that resists at least 4, 5, 6 and even 8 lbf are also contemplated by this invention. A plurality of watermelon plants grown in a field are also provided by the invention.

Any diploid or tetraploid inbred line having ultra firm flesh created from the teachings of this invention can transmit this ultra firm flesh phenotype to a hybrid. In addition to having ultra firm flesh at maturity, the watermelons of the present invention are capable of developing uniformly pigmented fruit flesh (red, yellow, or orange). In addition, at maturity, fruits from these inbred lines and hybrids will meet or exceed industry standards for sweetness, being at least good (not less than about 8 brix) and preferably very good (not less than about 10 brix).

The invention also provides a method for producing hybrid watermelon seed comprising crossing an inbred watermelon plant with a second watermelon plant and harvesting resultant hybrid watermelon seed, as well as a hybrid watermelon plant produced by growing the resultant hybrid watermelon seed.

The invention further provides a method for producing the ultra firm watermelon plant comprising the steps of crossing a watermelon variety having a level of sweetness that at least meets industry standards with a low sweetness watermelon variety having ultra firm flesh; performing at least one backcross with the variety having a level of sweetness that at least meet industry standards, and performing one or more cycles of self-pollination of products of the backcross (or recurrent backcross) having the combined traits of ultra firm flesh and sweetness that at least meets industry standards. The method may utilize as a watermelon having ultra firm flesh the watermelon plant of USDA Collection No. PI296341.

Watermelon fruit and watermelon flesh derived from the ultra-firm watermelon are also contemplated. Preferred are watermelon plants producing a fruit weighing at least about 1.5 kg, more preferably producing a fruit weighing at least about 3.0 kg. In a further preferred embodiment the watermelon plant produces a fruit weighing at least about 4.5 kg, and in a still further preferred embodiment the plant produces a fruit weighing at least about 6.0 kg.

The invention also provides a watermelon plant having the soluble solids and flesh firmness traits of a plant produced from seed deposited as Accession No. NCIMB 41230, made on Jul. 1, 2004, as well as seed, pollen, ovule and other vegetative tissue derived from the plant, or a watermelon plant regenerated from such tissue.

The invention also provides a watermelon plant with liquid-retaining flesh. As explained in detail below, this liquid-retaining trait corresponds to the amount of weight that cut watermelon fruit flesh loses over time. Preferred are watermelon plants wherein cut flesh from the watermelon fruit loses less than about three and one-half percent of its weight after three days storage at 4° centigrade. More preferred are such watermelon plants where the cut flesh loses less than about three percent weight after three days storage at 4° centigrade. A still further preferred watermelon plant is provided where the cut flesh loses less than about two percent weight after three days storage at 4° centigrade. In another preferred embodiment, the watermelon plant has cut flesh that loses less than about one and one-half percent weight after three days storage at 4° centigrade. This liquid-retaining trait extends the shelf life of processed watermelon fruit.

A preferred embodiment is a good ultra firm flesh watermelon diploid inbred line that produces sweet tasting mature fruit. Another preferred embodiment is a triploid hybrid, created using as at least one parental line that is either an ultra firm flesh diploid inbred line or an ultra firm flesh tetraploid inbred line that produces good standard sweet tasting mature fruit with ultra firm flesh. In another preferred embodiment the mature watermelon fruit produced in the diploid, tetraploid, or triploid plants of this invention develop full red flesh color and are sweet tasting, with good brix levels.

In yet another preferred embodiment, mature watermelon fruits of this invention develop full yellow flesh color and good sweetness in combination with ultra firm flesh. In still yet another preferred embodiment, the mature watermelon fruits of this invention develop full orange color and good sweetness in combination with ultra firm flesh. In another preferred embodiment the watermelon flesh from fruits of this invention stays ultra firm after being minimally processed (fresh cut fruit). This ultra firm feature extends the shelf life of the processed fruit.

The present invention also relates to a novel method of producing diploid and tetraploid watermelon lines and triploid watermelon hybrids that produce sweet tasting mature fruit with ultra firm flesh (resists pressure of at least 4.0 lbf; not less than 8 brix).

One step in this method involves crossing a known watermelon variety or line with a watermelon line of this invention having ultra firm flesh at maturity. The product of such cross is then self-pollinated to create a segregating population. In successive generations, individuals from populations segregating for the ultra firm flesh trait are subjected to successive cycles of selection and breeding and the end result is a new watermelon line that produces sweet tasting mature fruit having ultra firm flesh.

Certain embodiments of the present invention provide for unique watermelon plants with an ultra-firm flesh phenotype and their progeny. In certain embodiments, compositions and methods for producing, breeding, identifying, selecting, and the like of such plants or germplasm are provided. Novel plants of the present invention comprise an introgressed allele locus—located in a genomic region flanked by loci NW0251464 (SEQ ID NO: 1) and NW0250266 (SEQ ID NO: 18) —that is associated with the ultra-firm watermelon flesh phenotype. In certain embodiments, an introgressed allele locus associated with an ultra-firm watermelon flesh phenotype is one flanked by:
  a) loci NW0251464 (SEQ ID NO: 1) and NW0251011 (SEQ ID NO: 12);
  b) loci NW0251464 (SEQ ID NO: 1) and NW0252274 (SEQ ID NO: 10);
  c) loci NW0248953 (SEQ ID NO: 2) and NW0250266 (SEQ ID NO: 18);
  d) loci NW0248953 (SEQ ID NO: 2) and NW0251011 (SEQ ID NO: 12);
  e) loci NW0248953 (SEQ ID NO: 2) and NW0252274 (SEQ ID NO: 10);
  f) loci NW0250301 (SEQ ID NO: 3) and NW0250266 (SEQ ID NO: 18);
  g) loci NW0250301 (SEQ ID NO: 3) and NW0251011 (SEQ ID NO: 12); or
  h) loci NW0250301 (SEQ ID NO: 3) and NW0252274 (SEQ ID NO: 10).

The plants also comprise one or more polymorphic loci comprising alleles or combinations of alleles that are not found in an ultra-firm watermelon flesh variety and that are linked to the locus associated with an ultra-firm watermelon flesh phenotype. Thus, the introgressed allele locus is introduced into a background different from that of a previously existing ultra-firm watermelon flesh variety. In certain embodiments, the introgressed allele locus comprises at least one polymorphic nucleic acid selected from the group consisting of NW0248953 (SEQ ID NO: 2), NW0250301 (SEQ ID NO: 3), NW0248949 (SEQ ID NO: 4), NW0248646 (SEQ ID NO: 5), NW0249077 (SEQ ID NO: 6), NW0249132 (SEQ ID NO: 7), NW0252494 (SEQ ID NO: 8), NW0248163 (SEQ ID NO: 9), NW0252274 (SEQ ID NO: 10), NW0248905 (SEQ ID NO: 11), NW0251011 (SEQ ID NO: 12), NW0248869 (SEQ ID NO: 13), NW0251470 (SEQ ID NO: 14), NW0251308 (SEQ ID NO: 15), NW0250718 (SEQ ID NO: 16), and NW0248059 (SEQ ID NO: 17).

Certain embodiments provide for a method of identifying a watermelon plant with a genotype associated with an ultra-firm watermelon flesh phenotype. Such methods include detecting a genotype associated with an ultra-firm watermelon flesh phenotype in a watermelon plant. In certain embodiments a polymorphic nucleic acid is detected in a genomic region flanked by loci NW0251464 (SEQ ID NO: 1) and NW0250266 (SEQ ID NO: 18), or in a sub-region thereof as described herein. In certain embodiments, at least one polymorphic nucleic acid is selected from the group consisting of NW0248953 (SEQ ID NO: 2), NW0250301 (SEQ ID NO: 3), NW0248949 (SEQ ID NO: 4), NW0248646 (SEQ ID NO: 5), NW0249077 (SEQ ID NO: 6), NW0249132 (SEQ ID NO: 7), NW0252494 (SEQ ID NO: 8), NW0248163 (SEQ ID NO: 9), NW0252274 (SEQ ID NO: 10), NW0248905 (SEQ ID NO: 11), NW0251011 (SEQ ID NO: 12), NW0248869 (SEQ ID NO: 13), NW0251470 (SEQ ID NO: 14), NW0251308 (SEQ ID NO: 15), NW0250718 (SEQ ID NO: 16), and NW0248059 (SEQ ID NO: 17).

A watermelon plant that is identified having a genotype associated with an ultra-firm flesh watermelon phenotype can be denoted as comprising a genotype associated with an ultra-firm watermelon flesh phenotype. A watermelon plant, such as a denoted watermelon plant, comprising a genotype associated with an ultra-firm watermelon flesh phenotype can then be selected from a population of plants.

Certain embodiments of the invention provide for a method of producing a watermelon plant having in its genome an introgressed locus associated with an ultra-firm watermelon flesh phenotype. A watermelon plant lacking a locus associated with an ultra-firm watermelon flesh phenotype is crossed with a second watermelon plant that comprises: (a) an allele of at least one polymorphic nucleic acid that is associated with an ultra-firm watermelon flesh phenotype located in a genomic region flanked by loci NW0251464 (SEQ ID NO: 1) and NW0250266 (SEQ ID NO: 18) (or in a sub-region thereof as described herein), and (b) at least one additional polymorphic locus located outside of the region that is not present in said first watermelon plant. From this cross, a population of watermelon plants segregating for the polymorphic locus that is associated with an ultra-firm watermelon flesh phenotype and the additional polymorphic locus is obtained. The polymorphic locus that is associated with an ultra-firm watermelon flesh phenotype is detected in at least one watermelon plant of the population. A watermelon plant can then be selected having the locus associated with an ultra-firm watermelon flesh phenotype that lacks the additional polymorphic locus, thereby obtaining a watermelon plant that comprises in its genome at least one introgressed allele of a polymorphic nucleic acid associated with a firm watermelon flesh phenotype. In certain embodiments, at least one polymorphic nucleic acid is selected from the group consisting of NW0248953 (SEQ ID NO: 2), NW0250301 (SEQ ID NO: 3), NW0248949 (SEQ ID NO: 4), NW0248646 (SEQ ID NO: 5), NW0249077 (SEQ ID NO: 6), NW0249132 (SEQ ID NO: 7), NW0252494 (SEQ ID NO: 8), NW0248163 (SEQ ID NO: 9), NW0252274 (SEQ ID NO: 10), NW0248905 (SEQ ID NO: 11), NW0251011 (SEQ ID NO: 12), NW0248869 (SEQ ID NO: 13), NW0251470 (SEQ ID NO: 14), NW0251308 (SEQ ID NO: 15), NW0250718 (SEQ ID NO: 16), and NW0248059 (SEQ ID NO: 17).

Certain embodiments provide for a method of watermelon plant breeding. At least one watermelon that comprises at least one allele of a polymorphic nucleic acid that is genetically linked to a QTL that is flanked by loci NW0251464 (SEQ ID NO: 1) and NW0250266 (SEQ ID NO: 18) and associated with an ultra-firm watermelon flesh phenotype is selected. This watermelon plant is then crossed with itself or a second watermelon plant to produce progeny watermelon plants that have the QTL associated with an ultra-firm watermelon flesh phenotype. In certain embodiments, the at least one polymorphic nucleic acid that is genetically linked to the QTL is selected from the group consisting of NW0248953 (SEQ ID NO: 2), NW0250301 (SEQ ID NO: 3), NW0248949 (SEQ ID NO: 4), NW0248646 (SEQ ID NO: 5), NW0249077 (SEQ ID NO: 6), NW0249132 (SEQ ID NO: 7), NW0252494 (SEQ ID NO: 8), NW0248163 (SEQ ID NO: 9), NW0252274 (SEQ ID NO: 10), NW0248905 (SEQ ID NO: 11), NW0251011 (SEQ ID NO: 12), NW0248869 (SEQ ID NO: 13), NW0251470 (SEQ ID NO: 14), NW0251308 (SEQ ID NO: 15), NW0250718 (SEQ ID NO: 16), and NW0248059 (SEQ ID NO: 17).

Certain embodiments of the invention provide for a method of introgressing an allele into a watermelon plant. A population of watermelon plants is provided from which at least one watermelon plant is genotyped with respect to at least one polymorphic nucleic acid located in a genomic region flanked by loci NW0251464 (SEQ ID NO: 1) and NW0250266 (SEQ ID NO: 18). At least one watermelon plant is then selected from the population wherein the watermelon plant has at least one allele associated with an ultra-firm watermelon flesh phenotype. In certain embodiments, at least one polymorphic nucleic acid is selected from the group consisting of NW0248953 (SEQ ID NO: 2), NW0250301 (SEQ ID NO: 3), NW0248949 (SEQ ID NO: 4), NW0248646 (SEQ ID NO: 5), NW0249077 (SEQ ID NO: 6), NW0249132 (SEQ ID NO: 7), NW0252494 (SEQ ID NO: 8), NW0248163 (SEQ ID NO: 9), NW0252274 (SEQ ID NO: 10), NW0248905 (SEQ ID NO: 11), NW0251011 (SEQ ID NO: 12), NW0248869 (SEQ ID NO: 13), NW0251470 (SEQ ID NO: 14), NW0251308 (SEQ ID NO: 15), NW0250718 (SEQ ID NO: 16), and NW0248059 (SEQ ID NO: 17).

Certain embodiments of the invention provide for a watermelon plant obtained by any of the methods described herein capable of producing a watermelon plant such as by producing, breeding, introgressing, etc., or a progeny plant thereof. Certain embodiments of the invention are drawn to a part of such a plant including, but not limited to pollen, an ovule, a leaf, an embryo, a root, a root tip, an anther, a flower, a fruit, a stem, a shoot, a seed, a protoplast, a cell, or a callus from the plant. Certain embodiments of the invention are drawn to the seed of a watermelon plant obtained by any of the methods described herein capable of producing a watermelon plant such as by producing, breeding, introgressing, etc., or a seed of a progeny plant thereof.

Certain embodiments of the invention provide for an isolated nucleic acid probe or primer that hybridizes under conditions of 5×SSC, 50% formamide, and at 42° C. to a nucleic acid sequence selected from the group consisting of SEQ ID NOs: 1-18 or a fragment thereof, that contains a specific allelic variant. In certain embodiments, the probe or primer is at least 12 nucleotides in length. Certain embodiments of the invention provide for an isolated oligonucleotide comprising a nucleic acid molecule selected from the group consisting of SEQ ID NOs: 1, 2, 3, 4, 5, 6, 7, 8, 9, 10, 11, 12, 13, 14, 15, 16, 17, and 18, and any specific allelic variants thereof. Certain embodiments of the invention provide for an isolated oligonucleotide comprising a nucleic acid fragment of SEQ ID NOs: 1, 2, 3, 4, 5, 6, 7, 8, 9, 10, 11, 12, 13, 14, 15, 16, 17, or 18, that contains a specific allelic variant thereof and that is at least 12 nucleotides in length. Certain embodiments of the invention provide for an isolated oligonucleotide comprising a nucleic acid fragment of SEQ ID NOs: 1, 2, 3, 4, 5, 6, 7, 8, 9, 10, 11, 12, 13, 14, 15, 16, 17, or 18, that contains a specific allelic variant thereof, wherein the fragment that contains said allelic variant is at least 15, at least 18, at least 20, at least 22, at least 25, or at least 30 nucleotides in length.

Other objects, features and advantages of this invention will become apparent from the detailed description that follows. It should be understood that the detailed description and examples, while stating preferred embodiments of the invention, are by way of illustration only, as modifications and changes within the scope of the invention will become apparent to those skilled in the art.

DETAILED DESCRIPTION

Figure 1:
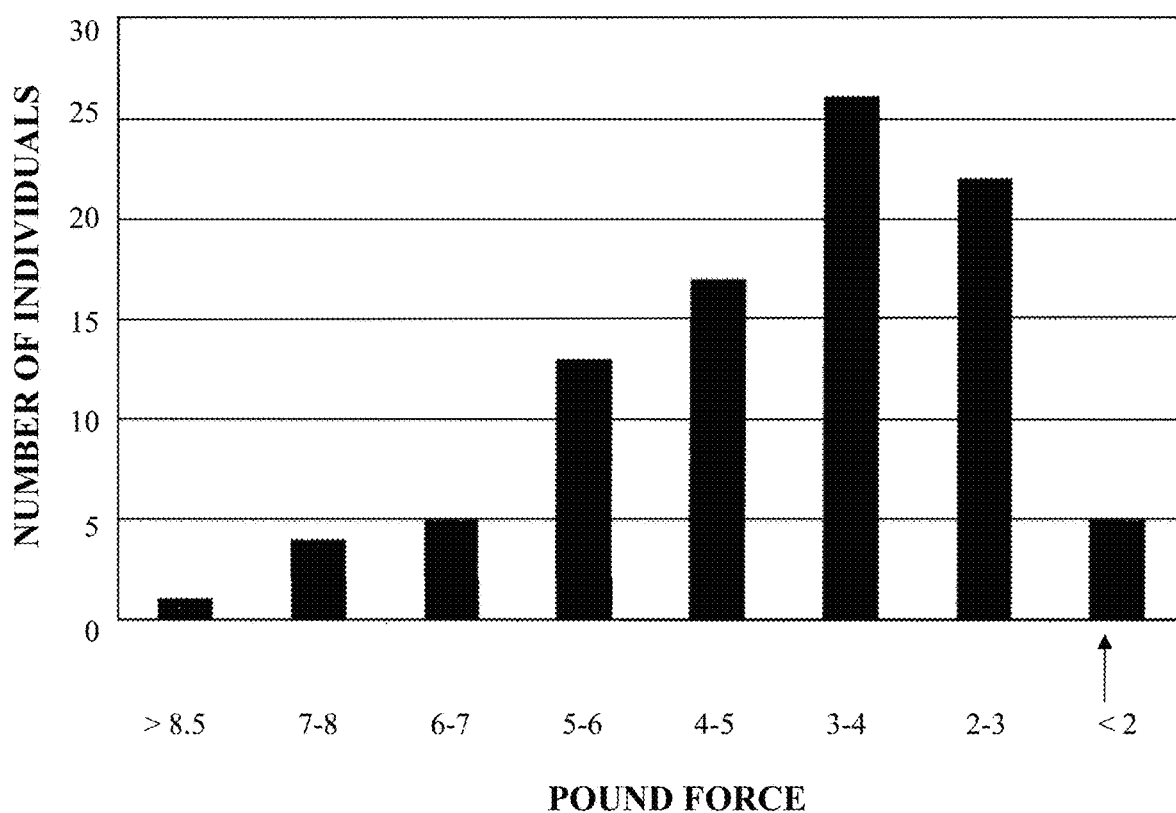
FIG. 1 is a histogram that illustrates fruit flesh firmness of the third generation of self-pollinated inbred watermelon plants of the present invention. The arrow indicates the average mature fruit firmness of the recurrent parent lines. The shaded portion of the histogram shows that 43% of these fruits have firmness readings at or above 4 lbf.

Headings are provided herein solely for ease of reading and should not be interpreted as limiting.

The present invention provides a watermelon plant that produces fruit with (i) ultra firm flesh and/or liquid-retaining flesh and (ii) sweetness of at least 6 brix. Therefore, the fruit of this invention have improved processing qualities, as, once cut, the fruit remains firm and/or retains its juice considerably longer than the commercial watermelon lines of the prior art.

Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which watermelon plants can be regenerated, plant calli, plant clumps and plant cells that are intact in plants or parts of plants such as pollen, flowers, seed, leaves, stems, and the like.

As used herein, having a watermelon "ultra-firm flesh phenotype" means that the edible flesh of a watermelon measures at least about 3.5 pounds force (lb/F) of pressure as evaluated with a penetrometer by methods described herein.

As used herein, "diploid plants" means plants or transplants derived from planting diploid seeds or from micropropagation that have two sets of chromosomes in the somatic cells, or twice the haploid number.

"Triploid plants" refers to plants or transplants derived from planting triploid seeds or from micropropagation that have three sets of chromosomes in the somatic cells, or three times the haploid number.

"Tetraploid plants" are plants or transplants derived from planting tetraploid seeds or from micropropagation that have four sets of chromosomes in the somatic cells, or four times the haploid number.

The term "firm flesh" refers to the edible flesh of a watermelon for which fruit firmness, as measured using a penetrometer by the methods described in Example 2, is greater than about 1.5 lbf of pressure but less than or equal to about 2.0 lbf. Botanically, the edible flesh of a watermelon fruit is placental tissue.

The descriptor "ultra firm flesh" refers to the edible flesh of a watermelon with fruit firmness, as measured using a penetrometer by the methods described in Example 2, measuring not less than 3.0 lbf of pressure, or with higher firmness than fruit produced by standard known cultivars. Ultra-firm flesh watermelon preferably has fruit firmness of about 3.5 lbf.

The term "very firm flesh" refers to the edible flesh of a watermelon with firmness, as measured using a penetrometer by the methods described in Example 2, greater than about 2.0 pound force of pressure but less than 3.0.

The term "liquid-retaining flesh" refers to edible flesh of a watermelon which, once cut, loses less than about four percent of its weight after three days storage at 4° centigrade, or retains more liquid, over time, than fruit produced by standard known cultivars. About 95-98% of the weight lost from cut watermelon fruit is estimated to be due to liquid leakage. The majority of the remaining weight loss is from soluble solids, such as sugars and acids. Therefore, liquid loss may be approximated by measuring the percent weight loss of watermelon fruit, once cut, over time.

A "penetrometer" is a device designed to measure force and is used herein to measure fruit firmness. It provides a quick, easy and accurate method to determine fruit flesh and skin firmness. Applicants gathered the data reported herein using a hand-held penetrometer to obtain three to five pressure readings on mature fruit. Specifically, Applicants used Penetrometer model FT011 (QA Supplies, Norfolk, Va.) with an 8 millimeter, or approximately 5/16 inch, probe.

"Pounds force", or "lbf", is the unit read by the penetrometer model FT011, and is used herein exclusively to indicate readings made using the 8 millimeter probe, unless otherwise indicated.

Coloration of the rind in watermelons, also referred to as "rind pattern", can vary from light green, often termed gray, to medium green, to very dark green, appearing to be almost black. In addition, the rind may have stripes of various designs which are typical of a variety or type. Therefore, the terms "tiger stripe", "mottle stripe", "dark mottle stripe", and the like, are used to identify various patterns.

As used herein, "length to width ratio (L/W ratio)" means the ratios obtained in any of the possible combinations by taking the average length divided by the average width on the watermelon fruit. The ratios can vary from 1:1.2 to 2.2:1.

The term "population" refers to a genetically heterogeneous collection of plants sharing a common parental derivation.

As used herein, the term "variety" or "cultivar" refers to a group of similar plants that, by their genetic pedigrees and performance, can be identified from other varieties within the same species.

"Backcrossing" refers to the process in which a breeder crosses a plant with one of its parent lines.

"Recurrent backcrossing" is a breeding strategy designed to recover the genetic composition of a line by crossing a plant in succession back to one of the parent lines.

The term "soluble solids" refers to the percent of solid material found in the edible portion of the fruit. As used herein, soluble solids are measured quantitatively with a refractometer as percentage brix. Refractometers often include a sucrose scale, as brix is formally defined as weight percent sucrose. If the only soluble solid present in an aqueous solution is sucrose, the sucrose scale should give the actual percentage sucrose. However, if other soluble solids are present, as is almost always the case, the reading is not equal to the percentage sucrose, but approximates the overall percentage of soluble solids in the sample. In short, although brix is technically defined as weight percent sucrose, those of skill in the art recognize that weight percent soluble solids, as obtained with a refractometer, approximates weight percent sucrose and accurately indicates sweetness. Therefore, the higher the percentage soluble solids, as indicated by brix level, the higher the perceived sweetness of the fruit.

As used herein, an "allele" refers to one of two or more alternative forms of a genomic sequence at a given locus on a chromosome.

A "Quantitative Trait Locus (QTL)" is a chromosomal location that encodes for alleles that affect the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, the term "introgressed," when used in reference to a genetic locus, refers to a genetic locus that has been introduced into a new genetic background. Introgression of a genetic locus can thus be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the term "linked," when used in the context of nucleic acid markers and/or genomic regions, means that the markers and/or genomic regions are located on the same linkage group or chromosome.

The U.S. Department of Agriculture has established watermelon fruit quality standards based on brix levels (United States Standards for Grades of Watermelon, U. S. Department of Agriculture (1978)). According to these standards and as used herein, edible parts of the fruit having not less than 8 brix are referred to as "good", while edible parts of the fruit having not less than 10 brix are referred to as "very good."

"Sweetness", as used herein, may be measured quantitatively, as described above, using a refractometer, or qualitatively, by taste.

A "quantitative trait loci", or "QTL" is a chromosomal location that encodes for alleles that affect the expressivity of a continuously distributed phenotype.

"Maturity" refers to maturity of fruit development and indicates the optimal time for harvest. Generally, growers of skill in the art harvest fruit at or substantially near its maximum sweetness and flavor intensity. In watermelon, the maturity comes associated with changes in rind appearance, flesh color and sugar content.

As used herein, the term "denoting" when used in reference to a plant genotype refers to any method whereby a plant is indicated to have a certain genotype. This includes any means of identification of a plant having a certain genotype. Indication of a certain genotype may include, but is not limited to, any entry into any type of written or electronic medium or database whereby the plant's genotype is provided. Indications of a certain genotype may also include, but are not limited to, any method where a plant is physically marked or tagged. Illustrative examples of physical marking or tags useful in the invention include, but are not limited to, a barcode, a radio-frequency identification (RFID), a label, or the like.

The terms "homozygous" and "homozygosity" are genetic terms. When identical alleles reside at corresponding loci on homologous chromosomes, that locus is called homozygous. Homozygosity typically refers to the degree to which a population is fixed at one or more loci.

A "hybrid" is an offspring of a cross between two genetically unlike individuals.

An "inbred" or "inbred line" is a substantially homozygous individual or variety.

"Introgress" is the process a breeder performs to introduce a new trait, usually from a non-cultivated type, into a cultivated type.

Successful watermelon production depends on attention to various cultural practices. These include soil management, with special attention to proper fertilization, crop establishment with appropriate spacing, weed control, the introduction of bees for pollination, irrigation, pest management, and, if producing fruit from triploid plants, a suitable pollen source for producing seedless (triploid) watermelon. Watermelon fruit size and shape, rind color, thickness and toughness, seed size, color, and number, flesh color, texture, sugar content, and freedom from fruit defects are all important characteristics to be considered in selection of watermelon varieties. Commercial seed companies typically offer the grower an opportunity to observe these characteristics in demonstration plots of their varieties, and some agricultural universities perform cultivar analysis data for the local growers (Roberts et al. (2004), Maynard and Sidoti (2003), Schultheis and Thompson (2004), and Leskovar et al. (2004).

Watermelon crops can be established from seed or from transplants. Transplanting is becoming more common because transplanting can result in an earlier crop compared with a crop produced from direct seeding. When a grower wants to raise a seedless fruited crop, transplanting is preferred. Transplanting helps achieve complete plant stands rapidly, especially where higher seed costs, as with triploid seeds, make direct-seeding risky.

Watermelon is the only economically important cucurbit with pinnatifid (lobed) leaves; all of the other species have whole (nonlobed) leaves. Watermelon growth habit is a trailing vine. The stems are thin, hairy, angular, grooved, and have branched tendrils at each node. The stems are highly branched and up to 30 feet long (Wehner et al. In: Watermelons: Characteristics, Production and Marketing. Maynard, editor. ASHS Press, Alexandria, Va. 2001).

Typical Characteristics of Commercial Watermelon Fruit

Watermelon breeders are challenged with anticipating changes in growing conditions, new pathogen pressure, and changing consumer preferences. With these projections, a breeder will attempt to create new cultivars that will fit the developing needs of growers, shippers, retailers, and consumers. Thus the breeder is challenged to combine in a single genotype as many favorable attributes as possible for good growing, distribution, and eating.

One important characteristic for the breeder is fruit size. Fruit size is an important consideration because there are different market requirements for particular groups of shippers and consumers. The general categories are: icebox (<12 lb), small (12-18 lb), medium (18-24 lb), large (24-32 lb), and giant (>32 lb). Fruit size is inherited in polygenic fashion, with an estimated 25 genes involved. Fruit is distributed from the grower to the retailer by shippers, who focus within particular weight categories, such as 18-24 lb for seeded and 14-18 lb for seedless. Although historic consumption has been for these general categories of sizes, there is an increasing trend in the marketplace for a new class of small-fruited watermelon hybrids (with fruit weight between 3-9 lb).

Fruit flesh firmness and liquid retention are other important characteristics. Consumers have varying textural preferences for watermelon fruit, and flesh firmness is a determinant of texture. Additionally, flesh firmness is a critical parameter that determines how long cut fruit will last on the retailer's shelf. Liquid retention is also critical to consumer perception of minimally processed watermelon. Cut fruit shelf life research is usually qualitative, with evaluations on when the "fruits become 'slimy'" (Perkins-Veazie et al. 1998 HortScience 33: 605). Quantitative evaluations of cut fruit shelf life include measuring the flesh firmness directly, using a penetrometer, or measuring percent weight loss of cut fruit over time in order to approximate liquid leakage, as described in Example 5.

Applicants were also able to determine the firmness of various fruit simply by eating them. Indeed, this was how applicants first determined that the watermelons of this invention have ultra firm flesh compared to prior art watermelons. In taste tests, Applicants also determined that standard cultivars of the prior art, such as *Seminis*' diploid Royal Star line, have firm flesh, while the following lines have firm to very firm flesh: Tri-X Brand 626 (Syngenta/Rogers—triploid), Extazy (Hazera—triploid) and Solitaire (Golden Valley—triploid).

Another important fruit characteristic is quality, which includes sweetness and attractiveness of fruit and rind color. Wehner et al. Watermelons: Characteristics, production and marketing. Maynard, editor. ASHS Press, Alexandria, Va. (2001). describe these characteristics. Among the most important of these characteristics is sweetness, without a bitter taste, which is measured by brix and by taste. Taste panel data demonstrated a direct correlation of good flavor scores with higher brix levels (Nip et al. (1968) *Proc. Amer. Soc. Hort. Sci.* 93:547). Brix levels increase as the fruit develops and ripens on the vine. Thus, immature fruits will have unacceptably low sweetness to the consumer; if picked too early, the edible tissue will also not have uniform color. Quantitative recommendations for watermelon fruits have been published. While Wehner et al. suggest brix levels between 10% and 14% brix, the United States Department of Agriculture (USDA) has established standards, as described in detail in the "Definitions" section, in which sweetness of at least 8 brix is good and sweetness of at least 10 brix is very good. Despite some variation in the recommendation and the standards, there is no dispute that fruit sweetness is a critical characteristic of watermelon fruit.

Characteristics of Watermelon Fruit of the Present Invention

Fruit Firmness

The flesh of watermelon plant fruits of the present invention is firmer and retains liquid better than the fruit flesh of watermelon cultivars of the prior art. In prior art watermelon fruit, mature edible flesh from diploid genotypes are softer than both triploid and tetraploid genotypes. Fruit firmness variation within a line, irrespective of ploidy level, is insignificant. In general, standard diploid cultivars produce fruits with soft to at best firm flesh (i.e., flesh firmness at maturity from less than 1.0 lbf to about 1.5 lbf). Standard tetraploid lines typically produce fruit with firm flesh or very firm flesh (i.e., flesh firmness between 1.5 lbf to less than about 3.0 lbf at maturity). Standard triploid hybrids produce seedless fruit with an intermediate level of flesh firmness at maturity, ranging from about 1.3 lbf to 2.5 lbf. Table 1 shows flesh firmness data from the prior art for commercial hybrids and inbred watermelon lines.

Firmness of watermelon flesh is an important fruit quality trait with several benefits for growers, processors, retailers, and customers. Watermelons with firmer flesh have increased field holding, allowing growers to harvest less frequently and/or harvest fruit at a more mature stage (85-95% maturity versus 70% of current market standard). They retain water, nutrients, and flavor during processing; thus having a higher fresh cut yield for processors, lower purge, and longer shelf-life for retailers and consumers. Current marketed watermelon products typically have a firmness of about 2 lb/F, while watermelons with an ultrafirm flesh phenotype have edible flesh that resists a pressure of at least 3.5 lb/F. Table 1 shows flesh firmness data from commercial hybrids and inbred lines.

All firmness measurements herein were made using a model FT011 penetrometer from QA Supplies in Norfolk, Va. with an 8 millimeter probe diameter. Readings were made and are reported in pounds force, a British Engineering measurement for pressure, which is abbreviated lbf and is converted to Newtons according to the following formula: 1 lbf=4.448 Newtons. Subject fruits were cut equatorially, midway between the blossom and stem ends of each fruit. Applicants made three to five readings per fruit, taking samples from the center of each cut fruit. Reported firmness data is an average of these three to five readings.

TABLE 1

Survey of firmness in typical watermelon cultivars and inbred lines. Average firmness readings are in pound force by methodology described herein.

| Line | Origin | Ploidy | Firmness |
| --- | --- | --- | --- |
| Tri-X 313 | Syngenta/Rogers | Triploid | 1.4 |
| Millionaire | Harris Moran | Triploid | 1.8 |
| Revolution | SunSeeds | Triploid | 1.7 |
| Majestic | Seminis | Triploid | 1.7 |
| Olympia | Seminis | Triploid | 1.6 |
| Omega | Seminis | Triploid | 1.5 |
| PS110-5288-9 | Seminis | Triploid | 2.3 |
| 4082 | Seminis | Tetraploid | 2 |
| 4084 | Seminis | Tetraploid | 1.5 |
| 4090 | Seminis | Tetraploid | 1.6 |
| 4133 | Seminis | Tetraploid | 2.2 |
| 4134 | Seminis | Tetraploid | 2.4 |
| 4135 | Seminis | Tetraploid | 2.2 |
| 4137 | Seminis | Tetraploid | 2.7 |
| 4138 | Seminis | Tetraploid | 2.2 |
| 47602A | Seminis | Diploid | 1.5 |
| 4203 | Seminis | Diploid | 1.4 |
| Cooperstown | Seminis | Triploid | 1.5 (Firm) |
| Fenway | Seminis | Triploid | 2.1 (Firm) |
| Royal Star | Seminis | Diploid | Firm |
| Sentinel | Seminis | Diploid | 1.4 (Firm) |
| Tri-X Brand 626 | Syngenta/Rogers | Diploid | Firm |
| W-1128 | Seminis | Diploid | 1.4 (Firm) |
| W-1119 | Seminis | Diploid | 1.6 (Firm) |
| BSI 2532 | Seminis | Diploid | 1.7 (Firm) |
| BSI 2527 | Seminis | Diploid | 1.3 (Firm) |
| W-2068 | Seminis | Diploid | 1.1 (Firm) |
| W-2741 | Seminis | Diploid | 1.3 (Firm) |
| W-1488 | Seminis | Diploid | 1.7 (Firm) |
| BSI 2543 | Seminis | Diploid | 1.2 (Firm) |
| Extazy | Hazera | Triploid | Firm |
| Solitaire | Golden Valley | Triploid | Firm |

Table 2 shows flesh firmness and sugar content from inbred line PI296341, and other various inbred lines created from PI296341 (see U.S. patent application Ser. No. 12/856, 286 which is incorporated herein by reference). PI29634 is resistant to *Fusarium* wilt, race 2 pathogen (*Fusarium oxysporum*), and is characterized by having very small round fruits between about 4 and about 6 inches in diameter and weighing between about 1 and about 2.6 pounds. Its fruit flesh is white, very firm, and having low sugars. Organoleptic evaluations of these fruits range from no perception of sweetness to bitter.

Compared to prior art watermelon lines, the fruit of the present invention both have ultra firm flesh and are sweet. Table 2 displays flesh firmness and sugar content from watermelon line PI296341, which was used as the source of the novel firm flesh fruit of this invention, and hybrid lines created according to the methods described herein. Sweetness measurements were determined quantitatively, using a refractometer (Leica Microsystems Model AR200, Reichert Inc., Depew, N.Y.), according to manufacturer's instructions. One measurement was taken from each half of an equatorially cut fruit. The data were recorded as an average.

As indicated by comparing the firmness readings in Table 2 to those in Table 1, the flesh of the watermelon fruit of the present invention is considerably more firm than the flesh of the watermelon fruit of the prior art. Specifically, watermelon fruit of the present invention resist pressure of at least about 3.0 lbf, preferably at least about 3.5 lbf, more preferably at least about 4 lbf and most preferably at least about 5 lbf.

In addition, as shown in Table 2, watermelon fruit of the present invention are sweet. Specifically, watermelon fruit display sweetness of at least about 6 brix, more preferably at least about 8 brix and most preferably at least about 10 brix.

TABLE 2

Firmness and sugar content of inbred and hybrid lines developed from the invention described herein and the PI296341 source. Firmness readings are in pound force and sugar content is reported as % Brix. Both measurement methods are described herein.

| Line | Origin | Ploidy | Firmness | Sugar content |
| --- | --- | --- | --- | --- |
| PI296341 | USDA collection | Diploid | 13.5 | 1.6 |
| 7132 | U.S. application Ser. No. 12/856, 286 | Triploid | 4.7 | 10.2 |
| 7133 | U.S. application Ser. No. 12/856, 286 | Triploid | 6.2 | 11.7 |
| 4201 | U.S. application Ser. No. 12/856, 286 | Diploid | 8.0 | 9.7 |
| 4203 | U.S. application Ser. No. 12/856, 286 | Diploid | 7.8 | 10.8 |
| 4204 | U.S. application Ser. No. 12/856, 286 | Diploid | 6.5 | 9.7 |
| 4207 | U.S. application Ser. No. 12/856, 286 | Diploid | 6.5 | 10 |

Liquid Retention

Figure 2:
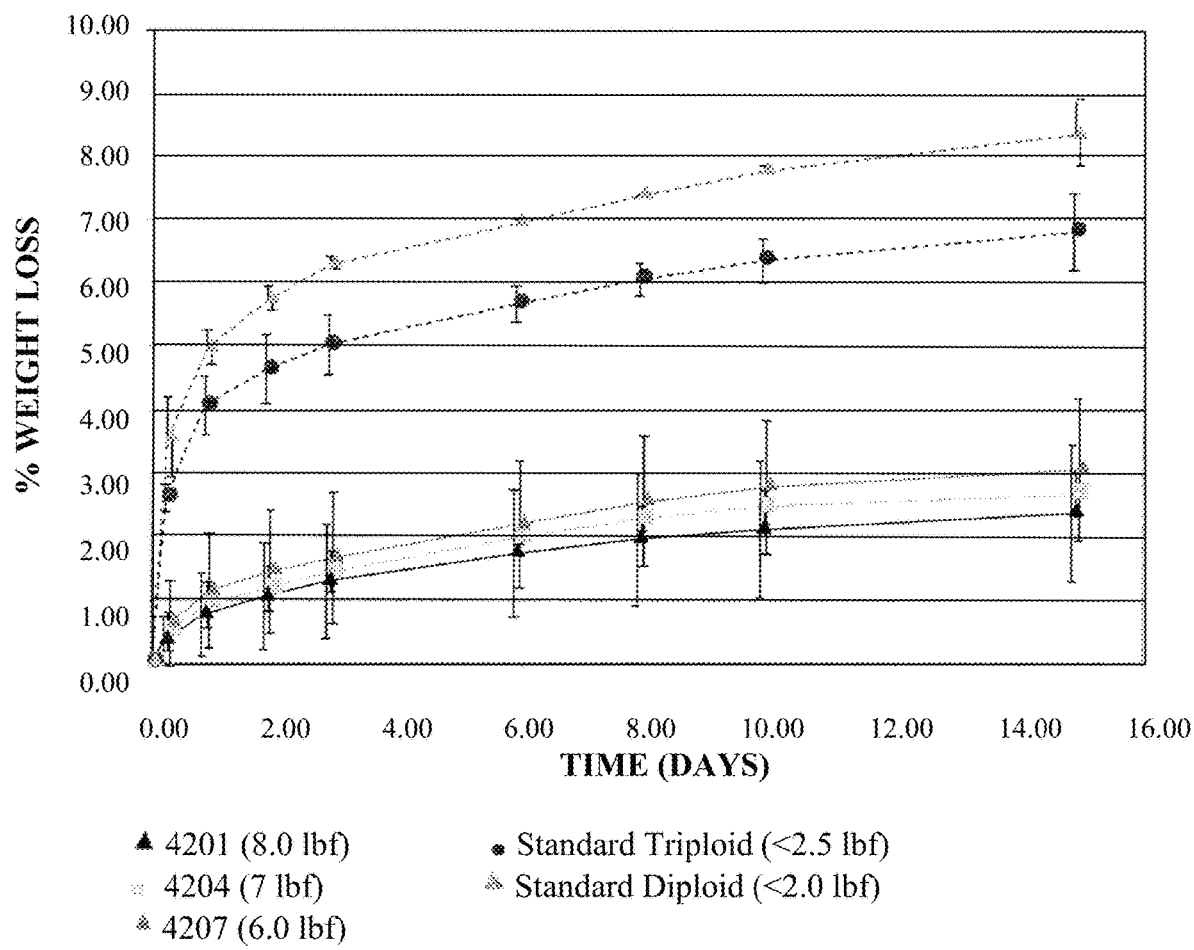
FIG. 2 is a graph showing weight loss after storage at 4° centigrade among processed fruit of standard commercial watermelon varieties and processed fruit of watermelon of the present invention. The weight loss closely approximates liquid leakage from the processed fruit.
Figure 3:
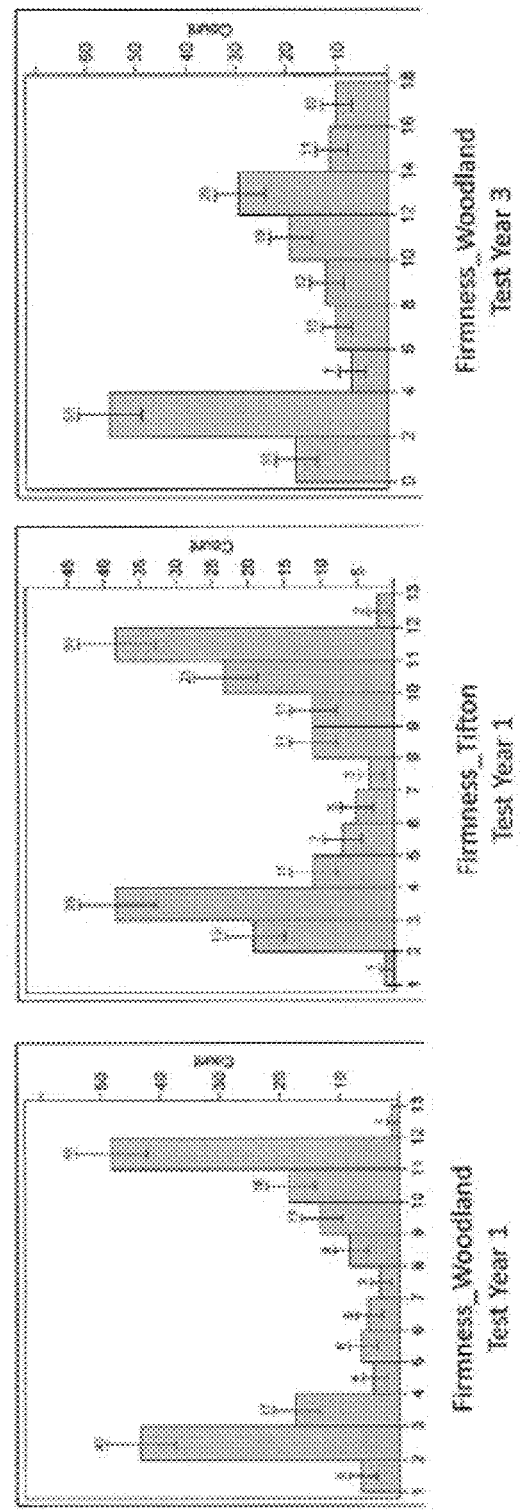
FIG. 3 shows the distributions of firmness phenotypes in three environments tested (Woodland, Calif. Test Year 1 and Test Year 3; Tifton, Ga. Test Year 1).

The fruit of the present invention also retain liquid better than the fruit of the prior art. Example 5 describes a study that demonstrates this liquid-retaining trait. The study compares liquid leakage rates of cut fruit from watermelon of this invention and of the prior art when stored at 4° centigrade. The results of this study are illustrated in FIG. 2. The study measures percent weight loss over time of cut fruit. This measurement approximates liquid loss, as 95-98% of the weight loss is due to liquid leakage. The remaining weight loss is due to leakage of other components of the fruit, such as soluble solids and acids. The primary conclusion from these data is that processed watermelon fruit of the present invention lose less liquid over time than processed fruit of standard known cultivars.

Watermelon fruit of the present invention lose less than about four percent weight after three days storage at 4° centigrade. Preferably, the fruit of the present invention lose less than about three and one-half percent weight after three days storage at 4° centigrade, more preferably less than about three percent weight, even more preferably less than about two percent weight, and most preferably less than about one and one-half percent weight. Watermelon fruit of the present invention also lose less than about five percent weight after a week of storage at 4° centigrade. Preferably, the fruit of the present invention lose less than about four percent weight after a week of storage at 4° centigrade, more preferably less than about three percent weight, even more preferably less than about two and one-half percent weight.

In addition to having liquid-retaining flesh, the fruit of the present invention are sweet. Specifically, these watermelon fruit display sweetness at least about 6 brix, more preferably at least about 8 brix and most preferably at least about 10 brix.

Other Traits

Watermelon plants of this invention may be seeded or seedless. Methods for obtaining diploid, triploid and tetraploid plants are well known in the art. Specifically, methods for obtaining diploid and triploid watermelon plants and seed of the present invention are described in detail below. Tetraploid plants of the present invention may be easily obtained by those of ordinary skill in the art using known cell biology techniques and the diploid plants described below.

Using standard crossing techniques, those of skill in the art may obtain watermelon fruit of the present invention with desirable traits besides those described above, as the ultra firm flesh and liquid-retaining flesh traits are dominantly inherited. For example, breeders may easily obtain watermelons of the present invention that are of a particular size or have a particular flesh color or rind pattern.

Breeding Techniques—Inbred and Hybrid Lines

Watermelon lines of the present invention were developed in the United States (Georgia, Florida and California), Mexico and Guatemala beginning in the year 2000. Furthermore, watermelon lines were grown for field performance and evaluation of adaptation in Florida, Georgia and California beginning in the year 2003. Additionally, diploid and diploid watermelon hybrids made with lines that produce watermelons having ultra firm flesh and/or liquid-retaining flesh at maturity were evaluated in field conditions in Florida, California and Mexico in 2003 and 2004. Specific crosses and firmness and quality evaluations of resultant fruits are described in detail in the "Examples" section.

For most breeding objectives, commercial breeders work with germplasm that is often referred to as the "cultivated type." This germplasm is easier to breed with because it generally performs well when evaluated for horticultural performance. The performance advantage the cultivated types provide is sometimes offset by a lack of allelic diversity. This is the tradeoff a breeder accepts when working with cultivated germplasm—better overall performance, but a lack of allelic diversity. Breeders generally accept this tradeoff because progress is faster when working with cultivated material than when breeding with genetically diverse sources.

In contrast, when a breeder makes either wide intra-specific crosses, or inter-specific crosses, a converse tradeoff occurs. In these examples, a breeder typically crosses cultivated germplasm with a non-cultivated type. In these crosses, the breeder can gain access to novel alleles from the non-cultivated type, but has to overcome the genetic drag associated with the donor parent. Because of the difficulty with this breeding strategy, this approach often fails because of fertility or fecundity problems. The difficulty with this breeding approach extends to many crops, and is exemplified with an important disease resistant phenotype that was first described in tomato in 1944 (Smith, Proc. Am. Soc. Hort. Sci. 44:413-416). In this cross, a nematode disease resistance was transferred from *L. peruvianum* (PI128657) into a cultivated tomato. Despite intensive breeding, it was not until the mid-1970's before breeders could overcome the genetic drag and release successful lines carrying this trait. Indeed, even today, tomato breeders deliver this disease resistance gene to a hybrid variety from only one parent. This allows the remaining genetic drag to be masked. The inventiveness of succeeding in this breeding approach has been recognized by the USPTO (U.S. Pat. Nos. 6,414,226, 6,096,944, 5,866,764, and 6,639,132).

In watermelon, the plant introduction (PI) accessions are typically lines that produce small fruits with firm white flesh and very poor taste (even bitter). Even though these lines have such poor horticultural qualities, some watermelon breeders, like some other crop breeders, attempt to breed with these PI lines because they potentially contain novel alleles. To date, the most commonly attempted breeding objective for use of the PI line series is to introgress new disease resistance genes. The process of introgressing novel resistance genes from the PI lines into acceptable commercial types is a long and often arduous process. This process can be difficult because the trait may be polygenic, have low heritability, have linkage drag or some combination of the three.

This breeding project began with a wide cross between cultivated watermelons and PI No. 296341, which was obtained from the USDA collection at the Regional Plant Introduction Station in Griffin, Ga. This accession has been available to watermelon breeders since its deposit into the U.S. Plant Introduction system in 1964.

The original intent of the project, however, was not to make watermelon fruit with firm flesh and/or liquid-retaining flesh. Rather, the original intent of the project was to introgress a resistance to *Fusarium* wilt, specifically to *Fusarium oxysporum* f. sp. *niveum* race 2, referred to herein as FON race 2. Although no commercial watermelons currently contain resistance to FON race 2, the possibility of using PI296341 as a source of resistance has been known for many years (Netzer (1989) *Plant Disease* 73:518; Martyn and Netzer (1991) *HortScience* 26:429-432; Wehner et al. ((2001) in: Watermelons: Characteristics, production and marketing. Maynard, editor. ASHS Press. Alexandria, Va.). That there are no watermelon commercial lines for sale with FON race 2 resistance introgressed from PI296341, despite these reports as long as 15 years ago, underscores the difficulty of introgressing traits from wide crosses and creating commercially successful inbreds and hybrids.

In addition to being resistant to FON race 2, PI296341 is characterized by having very small round fruits between 4 and 6 inches in diameter and weighing between 1 and 2.6 pounds. Fruit flesh is white and very firm, with low soluble solids content (Table 2). Organoleptic evaluations of these fruits range from no perception of sweetness to bitter. As described in the "Examples" section below, inbred watermelon plants of the present invention may be obtained by crossing a watermelon with the ultra firm flesh trait and/or liquid-retaining flesh trait (ultra firm parent) with a non-ultra firm flesh watermelon with other desirable quality characteristics, including sweetness (recurrent parent). The ultra firm parent may be plant introduction accession number 296341.

Those of skill in the art will be able to introgress the ultra firm flesh trait and/or the liquid-retaining trait into the recurrent parent by conducting various recurrent back-crosses, selecting for the (i) ultra firm flesh and/or liquid-retaining flesh trait and (ii) the sweetness trait, and finally self-pollinating selected plants of the recurrent backcrosses to create inbred watermelon lines with the above traits. One possible method for accomplishing such introgression is described in the "Examples" section below.

Applicants generated inbred line 3347, which generates sweet ultra firm fruit according to the present invention, using the methods described above and in the "Examples" section. See, especially, Example 6. Inbred line 3347 has been deposited with NCIMB and accorded Accession No. NCIMB 41230. Details of the deposit follow the "Examples" section.

Using known methods, breeders may obtain diploid, triploid and tetraploid inbred lines of watermelon having fruit with the (i) ultra firm flesh and/or liquid-retaining flesh trait and (ii) sweetness trait.

In addition, because the ultra firm flesh and liquid-retaining traits of the present invention are dominantly inherited, breeders may obtain hybrids using the watermelons of this invention. Hybrids may be either diploid or triploid. Specifically, breeders crossed inbred watermelon plants with the above desired flesh traits and sweetness traits to either diploid or tetraploid non-ultra firm flesh cultivars to create, respectively, diploid or triploid watermelon plants with fruit having the ultra firm flesh and/or liquid-retaining flesh trait and sweetness trait. The non-ultra firm flesh parent used in creating a hybrid may also be used to obtain sweet ultra firm flesh and/or liquid-retaining flesh watermelon with other desirable traits, such as a particular size and/or color.

Those skilled in the art recognize that there are several breeding methods used for the introgression of new traits into commercial germplasm, including mass selection, pedigree selection, recurrent selection and backcrossing. By way of example, and by no means limiting, the introgression of ultra firm flesh watermelon fruit at maturity, with high brix levels is described below.

It is reported herein that a quantitative trait locus (QTL) with major effects for firmness and single nucleotide polymorphism (SNP) markers in the proximity of this locus have been identified that can be used for the introgression of this genomic region to desirable germplasm, such as by marker-assisted selection and/or marker-assisted backcrossing. A population of plants was obtained from a cross between the watermelon lines 03LB3378-1 and WAS-35-2438. From this population, a linkage map consisting of 19 linkage groups was constructed using 404 polymorphic markers. QTL mapping analysis revealed a major locus controlling flesh firmness on the proximal end of linkage group 9. This discovery of a major firmness QTL will facilitate the development of ultra-firm flesh watermelon products.

Certain embodiments of the present invention provide for watermelon plants comprising in their genome an introgressed allele locus associated with an ultra-firm watermelon flesh phenotype wherein the introgressed locus allele has not previously been introgressed into the genomic background of a specific variety or cultivar. Certain embodiments provide for methods of detecting in a watermelon plant a genotype associated with an ultra-firm flesh phenotype in a watermelon plant. Certain embodiments provide for methods of identifying and selecting a watermelon plant comprising in its genome a genotype associated with an ultra-firm flesh phenotype. Further, certain embodiments provide for methods of producing a watermelon plant that comprises in its genome at least one introgressed locus associated with an ultra-firm flesh phenotype and methods for introgressing such an allele into a watermelon plant. Watermelon plants and parts thereof made by any of said methods are also provided for in certain embodiments of the invention as well as polymorphic nucleic acid sequences.

The use of markers to infer a phenotype of interest results in the economization of a breeding program by substituting costly, time-intensive phenotyping assays with genotyping. Further, breeding programs can be designed to explicitly drive the frequency of specific favorable phenotypes by targeting particular genotypes (U.S. Pat. No. 6,399,855). Fidelity of these associations may be monitored continuously to ensure maintained predictive ability and, thus, informed breeding decisions (U.S. Patent Pub. No. 2005/0015827).

Genomic Region, QTL, Polymorphic Nucleic Acids, and Alleles Associated with an Ultra-Firm Watermelon Flesh Phenotype Applicants have discovered a genomic region, QTL, alleles, polymorphic nucleic acids, linked markers, and the like that when present in certain allelic forms are associated with the ultra-firm watermelon flesh phenotype. The genomic region is located at the proximal end of watermelon linkage group 9 (of the genetic map of the 03LB3378-1× WAS-35-2438 population) and flanked by loci NW0251464 (SEQ ID NO: 1) and NW0250266 (SEQ ID NO: 18). A major watermelon flesh firmness QTL was found to be located within this region. Certain of the various embodiments of the invention utilize a QTL or polymorphic nucleic acid marker or allele located in this genomic region. Sub-regions of this genomic region associated with an ultra-firm watermelon flesh phenotype can be described as being flanked by:

a) loci NW0251464 (SEQ ID NO: 1) and NW0251011 (SEQ ID NO: 12);
b) loci NW0251464 (SEQ ID NO: 1) and NW0252274 (SEQ ID NO: 10);
c) loci NW0248953 (SEQ ID NO: 2) and NW0250266 (SEQ ID NO: 18);
d) loci NW0248953 (SEQ ID NO: 2) and NW0251011 (SEQ ID NO: 12);
e) loci NW0248953 (SEQ ID NO: 2) and NW0252274 (SEQ ID NO: 10);
f) loci NW0250301 (SEQ ID NO: 3) and NW0250266 (SEQ ID NO: 18);
g) loci NW0250301 (SEQ ID NO: 3) and NW0251011 (SEQ ID NO: 12); or
h) loci NW0250301 (SEQ ID NO: 3) and NW0252274 (SEQ ID NO: 10).

Certain of the various embodiments of the invention utilize a QTL or polymorphic nucleic acid marker or allele located in one or more of these subregions.

Polymorphic nucleic acid markers located within the region flanked by loci NW0251464 (SEQ ID NO: 1) and NW0250266 (SEQ ID NO: 18) include, but are not limited to: NW0248953 (SEQ ID NO: 2), NW0250301 (SEQ ID NO: 3), NW0248949 (SEQ ID NO: 4), NW0248646 (SEQ ID NO: 5), NW0249077 (SEQ ID NO: 6), NW0249132 (SEQ ID NO: 7), NW0252494 (SEQ ID NO: 8), NW0248163 (SEQ ID NO: 9), NW0252274 (SEQ ID NO: 10), NW0248905 (SEQ ID NO: 11), NW0251011 (SEQ ID NO: 12), NW0248869 (SEQ ID NO: 13), NW0251470 (SEQ ID NO: 14), NW0251308 (SEQ ID NO: 15), NW0250718 (SEQ ID NO: 16), and NW0248059 (SEQ ID NO: 17). Such markers are believed to be associated with the ultra-firm watermelon flesh phenotype because of their location and proximity to the major firmness QTL. Certain of the various embodiments of the invention utilize one or more polymorphic nucleic acids selected from this group. In certain embodiments, at least two of such markers are used.

The peak of the QTL was found to be in close proximity to at least NW0249132 (SEQ ID NO: 7), NW0248163 (SEQ ID NO: 9), NW0251011 (SEQ ID NO: 12), and NW0250266 (SEQ ID NO:18). To date, NW0250301 (SEQ ID NO: 3), NW0248646 (SEQ ID NO: 5), and NW0252274 (SEQ ID NO:10) have been validated as predictive of the ultra-firm flesh phenotype in diverse watermelon germplasm. In certain of the various embodiments of the invention, at least one polymorphic nucleic acid selected from the group consisting of NW0250301 (SEQ ID NO: 3), NW0248646 (SEQ ID NO: 5), and NW0252274 (SEQ ID NO: 10) is used. In certain embodiments, at least two polymorphic nucleic acids selected from this group are used. In certain embodiments, at least all three of NW0250301 (SEQ ID NO: 3), NW0248646 (SEQ ID NO: 5), and NW0252274 (SEQ ID NO: 10) are used.

In certain embodiments of the invention, it is useful to detect in, or determine whether, a watermelon plant has an allelic state that is associated with an ultra-firm flesh phenotype (Table 3). In certain other embodiments, it is useful to detect in, or determine whether, a watermelon plant has an allelic state that is not associated with an ultra-firm flesh phenotype (Table 3) (The position of the polymorphic site identified in Table 3 for each of these marker sequences is contained in Table 10 and the accompanying Sequence Listing).

In certain embodiments, a plant is identified in which at least one allele at a polymorphic locus associated with an ultra-firm watermelon flesh phenotype is detected. For example, a diploid plant in which the allelic state at a polymorphic locus comprises one allele associated with an ultra-firm watermelon flesh phenotype and one allele that is not associated with an ultra-firm flesh phenotype (i.e., heterozygous at that locus). In certain embodiments of the invention, it may be useful to cross a plant that is heterozygous at a locus associated with an ultra-firm flesh phenotype with a plant that is similarly heterozygous or that does not contain any allele associated with an ultra-firm flesh phenotype at the locus, to produce progeny a certain percentage of plants that are heterozygous at that locus. Plants homozygous at the locus may then be produced by various breeding methods, such as by self-crossing or dihaploidization. In another example, a triploid or tetraploid watermelon plant is identified in which the allelic state at a locus comprises at least one allele associated with an ultra-firm watermelon flesh phenotype wherein other alleles of the locus may or may not also be an allele associated with an ultra-firm watermelon flesh phenotype. Non-limiting exemplary examples include identifying a plant that: has at least one allele of the C allelic state of the polymorphic nucleic acid of NW0252274 (SEQ ID NO: 10); has at least one allele of the C allelic state of the polymorphic nucleic acid of NW0248646 (SEQ ID NO: 5); or has at least one allele of the G allelic state of the polymorphic nucleic acid of NW0250301 (SEQ ID NO: 3); any combination of two of these allelic states, or comprising all three. Certain embodiments include identifying a watermelon plant that: is a diploid plant having one allele of the C allelic state of the polymorphic nucleic acid of NW0252274 (SEQ ID NO: 10) and one allele of the T allelic state of the polymorphic nucleic acid of NW0252274 (SEQ ID NO: 10); is a diploid plant having one allele of the C allelic state of the polymorphic nucleic acid of NW0248646 (SEQ ID NO: 5) and one allele of the A allelic state of the polymorphic nucleic acid of NW0248646 (SEQ ID NO: 5); or is a diploid plant having one allele of the G allelic state of the polymorphic nucleic acid of NW0250301 (SEQ ID NO: 3) and one allele of the A allelic state of the polymorphic nucleic acid of NW0250301 (SEQ ID NO: 3); any combination of two of these allelic states, or comprising all three. One of skill in the art will also recognize that it can be useful to identify at a genetic locus a polymorphic nucleic acid marker that is not associated with an ultra-firm watermelon flesh phenotype in a plant, such as when introgressing a QTL associated with an ultra-firm watermelon flesh phenotype into a genetic background not associated with such a phenotype.

In certain embodiments, a plant is identified in which at least two alleles associated with an ultra-firm watermelon flesh phenotype at a locus are detected. For example, a diploid plant in which both allelic states at a polymorphic locus are associated with an ultra-firm watermelon flesh phenotype (i.e., homozygous at that locus). For example, a triploid or tetraploid watermelon plant in which the allelic state comprises at least two alleles at a locus that are associated with an ultra-firm watermelon flesh phenotype, wherein other alleles at the locus may or may not also be an allele associated with an ultra-firm watermelon flesh phenotype. Certain non-limiting exemplary examples include identifying: a diploid watermelon plant that has the CC allelic state of the polymorphic nucleic acid of NW0248646 (SEQ ID NO: 5); a diploid watermelon plant that has the CC allelic state of the polymorphic nucleic acid of NW0248646 (SEQ ID NO: 5); or a diploid watermelon plant that has the GG allelic state of the polymorphic nucleic acid of NW0250301 (SEQ ID NO: 3); any combination of two of these allelic states, or the plant comprises all three.

The above markers and allelic states are exemplary. From Table 3, one of skill in the art would recognize how to identify watermelon plants with other polymorphic nucleic acid markers and allelic states thereof related to watermelon firmness consistent with the present invention. One of skill the art would also know how to identify the allelic state of other polymorphic nucleic acid markers located in the genomic region(s) or linked to the QTL or other markers identified herein, to determine their association with watermelon firmness.

TABLE 3

Genetic positions* and alternate allelic states of polymorphic nucleic acid markers of the invention indicating the allelic state associated with the ultra-firm watermelon flesh QTL.

| Marker Name | SEQ ID NO: | Linkage Group | Genetic Map position (cM) | Allele 1 (non-firm flesh) | Allele 2 (ultra-firm flesh phenotype QTL-associated) |
|---|---|---|---|---|---|
| NW0251464 | 1 | 2 | 122.4666304 | A or G | deletion, absence of allele |
| NW0248953 | 2 | 2 | 131.6920961 | A | T |
| NW0250301 | 3 | 2 | 134.2525663 | A | G |
| NW0248949 | 4 | 2 | 136.2284633 | G | A |
| NW0248646 | 5 | 2 | 136.9855946 | A | C |
| NW0249077 | 6 | 2 | 136.9855946 | A or C | deletion, absence of allele |
| NW0249132 | 7 | 2 | 136.9920737 | T or C | deletion, absence of allele |
| NW0252494 | 8 | 2 | 137.6844216 | T or C | deletion, absence of allele |
| NW0248163 | 9 | 2 | 138.2842599 | A or C | deletion, absence of allele |
| NW0252274 | 10 | 2 | 138.5377262 | T | C |
| NW0248905 | 11 | 2 | 138.7747985 | A | G |
| NW0251011 | 12 | 2 | 138.7747985 | C | T |
| NW0248869 | 13 | 2 | 139.8297546 | T | G |
| NW0251470 | 14 | 2 | 139.8297546 | A | T |
| NW0251308 | 15 | 2 | 144.5711848 | C | T |
| NW0250718 | 16 | 2 | 145.8088579 | C | T |
| NW0248059 | 17 | 2 | 152.2083556 | G | A |
| NW0250266 | 18 | 2 | 157.6817827 | T | C |

*Linkage group 9 from the genetic map of the 03LB3378-1 × WAS-35-2438 derived population was aligned to linkage group 2 of a consensus watermelon SNP map constructed with three additional segregating populations. In Table 9, the genetic map positions represent positions on linkage group 2 of the consensus watermelon SNP map.

Like humans, watermelons are natural diploids, having their chromosomes arranged in pairs. Watermelon plants, however, can undergo a duplication of their entire set of chromosomes and exist as tetraploids. While it is uncommon for watermelons to produce spontaneous tetraploids, this process can be routinely produced in the laboratory using cell biology techniques. Triploid seeds can be produced by crossing a tetraploid parent by a diploid parent. When triploid plants are grown, seed formation in the fruit aborts because of the ploidy level differences, resulting in seedless fruits.

In certain embodiments of methods of the invention, a male parent diploid plant is homozygous for the QTL or a polymorphic nucleic acid marker allele associated with the firm watermelon flesh phenotype. The male parent diploid is crossed with a female tetraploid lacking the QTL or a polymorphic nucleic acid marker allele associated with the firm watermelon flesh phenotype, to produce triploid hybrid progeny. This results in one copy of the QTL or polymorphic marker allele associated with the firm watermelon flesh phenotype (from the diploid parent) and two non-QTL/ marker alleles (from the tetraploid parent) in the triploid hybrid.

Certain embodiments of the invention contemplate the use of dihaploidization to produce an inbred line. A haploid plant has only one copy of each chromosome instead of the normal pair of chromosomes in a diploid plant. Haploid plants can be produced, for example, by treating with a haploid inducer. Haploids plants can be subjected to treatment that causes the single copy chromosome set to double, producing a duplicate copy of the original set. The resulting plant is termed a "double-haploid" and contains pairs of chromosomes that are generally in a homozygous allelic state at any given locus. Dihaploidization can reduce the time required to develop new inbred lines in comparison to developing lines through successive rounds of backcrossing.

As used herein, in a diploid plant, a homozygous allelic state is represented as AA, CC, GG, or TT, where the designated polymorphic position of the allele comprises alternate nucleotide bases. As used herein, in a diploid plant, a homozygous allelic state is represented as DD, where the designated polymorphic position of the allele comprises a deletion of one or more bases in comparison to an alternate allele.

One of skill in the art would understand that additional polymorphic nucleic acids that are located in the genomic regions identified may be used in certain embodiments of the methods of the invention. Given the provisions herein of a genomic region, QTL, and polymorphic markers identified herein, additional markers located either within or near this genomic region that are associated with the phenotype can be obtained by typing new markers in various germplasm. The genomic region, QTL, and polymorphic markers identified herein can also be mapped relative to any publically available physical or genetic map to place the region described herein on such map. One of skill in the art would also understand that additional polymorphic nucleic acids that are genetically linked to the QTL associated with a firm watermelon flesh phenotype and that map within 40 cM, 20 cM, 10 cM, 5 cM, or 1 cM of the QTL associated with a firm watermelon flesh phenotype may also be used.

Introgression of a Genomic Locus Associated with a Firm Flesh Phenotype

Provided herein are unique watermelon germplasms or watermelon plants comprising an introgressed genomic region that is associated with a firm watermelon flesh phenotype and method of obtaining the same. Marker-assisted introgression involves the transfer of a chromosomal region, defined by one or more markers, from one germplasm to a second germplasm. Offspring of a cross that contain the introgressed genomic region can be identified by the combination of markers characteristic of the desired introgressed genomic region from a first germplasm (e.g., a firm watermelon flesh phenotype germplasm) and both linked and unlinked markers characteristic of the desired genetic background of a second germplasm. Flanking markers that identify a genomic region associated with a firm watermelon flesh phenotype are loci NW0251464 (SEQ ID NO: 1) and NW0250266 (SEQ ID NO: 18), and those that identify sub-regions thereof include, but are not limited to:
 a) loci NW0251464 (SEQ ID NO: 1) and NW0251011 (SEQ ID NO: 12);
 b) loci NW0251464 (SEQ ID NO: 1) and NW0252274 (SEQ ID NO: 10);
 c) loci NW0248953 (SEQ ID NO: 2) and NW0250266 (SEQ ID NO: 18);
 d) loci NW0248953 (SEQ ID NO: 2) and NW0251011 (SEQ ID NO: 12);
 e) loci NW0248953 (SEQ ID NO: 2) and NW0252274 (SEQ ID NO: 10);
 f) loci NW0250301 (SEQ ID NO: 3) and NW0250266 (SEQ ID NO: 18);
 g) loci NW0250301 (SEQ ID NO: 3) and NW0251011 (SEQ ID NO: 12); and
 h) loci NW0250301 (SEQ ID NO: 3) and NW0252274 (SEQ ID NO: 10).

Flanking markers that fall on both the telomere proximal end and the centromere proximal end (such as those provided herein) of any of these genomic intervals may be useful in a variety of breeding efforts that include, but are not limited to, introgression of genomic regions associated with an ultra-firm watermelon flesh phenotype into a genetic background comprising markers associated with germplasm that ordinarily contains a genotype associated with a non-firm flesh phenotype. Markers that are linked and either immediately adjacent or adjacent to the identified ultra-firm watermelon flesh phenotype QTL that permit introgression of the QTL in the absence of extraneous linked DNA from the source germplasm containing the QTL are provided herewith. Those of skill in the art will appreciate that when seeking to introgress a smaller genomic region comprising a QTL associated with an ultra-firm watermelon flesh phenotype described herein, that any of the telomere proximal or centromere proximal markers that are immediately adjacent to a larger genomic region comprising the QTL can be used to introgress that smaller genomic region.

Watermelon plants or germplasm comprising an introgressed region that is associated with an ultra-firm watermelon flesh phenotype wherein at least 10%, 25%, 50%, 75%, 90%, or 99% of the remaining genomic sequences carry markers characteristic of plant or germplasm that otherwise or ordinarily comprise a genomic region associated with an non-ultra-firm flesh phenotype, are thus provided. Furthermore, watermelon plants comprising an introgressed region where closely linked regions adjacent and/or immediately adjacent to the genomic regions, QTL, and markers provided herewith that comprise genomic sequences carrying markers characteristic of watermelon plants or germplasm that otherwise or ordinarily comprise a genomic region associated with the phenotype are also provided.

Molecular Assisted Breeding Technique

Genetic markers that can be used in the practice of the present invention include, but are not limited to, Restriction Fragment Length Polymorphisms (RFLP), Amplified Fragment Length Polymorphisms (AFLP), Simple Sequence Repeats (SSR), Single Nucleotide Polymorphisms (SNP), Insertion/Deletion Polymorphisms (Indels), Variable Number Tandem Repeats (VNTR), and Random Amplified Polymorphic DNA (RAPD), and others known to those skilled in the art. Marker discovery and development in crops provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

As a set, polymorphic markers serve as a useful tool for fingerprinting plants to inform the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a watermelon plant a genotype associated with a firm watermelon flesh phenotype, identify a watermelon plant with a genotype associated with a firm watermelon flesh phenotype, and to select a watermelon plant with a genotype associated with a firm watermelon flesh phenotype. In certain embodiments of methods of the invention, polymorphic nucleic acids can be used to produce a watermelon plant that comprises in its genome an introgressed locus associated with a firm watermelon flesh phenotype. In certain embodiments of the invention, polymorphic nucleic acids can be used to breed progeny watermelon plants comprising a locus associated with a firm watermelon flesh phenotype.

Certain genetic markers useful in the present invention include "dominant" or "codominant" markers. "Codominant" markers reveal the presence of two or more alleles (two per diploid individual). "Dominant" markers reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

Nucleic acid-based analyses for determining the presence or absence of the genetic polymorphism (i.e., for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with a firm watermelon flesh phenotype.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201,184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entireties. However, the compositions and methods of the present invention can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by R.F. Service Science 2006 311:1544-1546.

The markers to be used in the methods of the present invention should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTLs.

EXAMPLES

Example 1

Generation of F1 Lines and Backcrosses

In the summer of 2000, four first filial (F1) generation lines were created by crossing 4 *Seminis* inbred lines as females to PI296341. The four diploid inbred lines used were W-2388, W-1128, W-1119 and W-1488. Line W-2388 is elongated in shape with a length to width (L/W) ratio of 1.8 to 2.2:1. The rind color and pattern is of medium green background with wide darker stripes. This shape and rind pattern phenotype is known to those skilled in the art as an "elongated dark mottle stripe" watermelon fruit. The fruit shape of Line W-1128 is round oval with L/W ratio of 1.0-1.2:1 and rind color is of light to medium green background and narrow darker green stripes. This phenotype is known to those skilled in the art as "round-oval with narrow (or tiger) stripes" watermelon fruit. Fruit shape of Line W-1119 is oval to high round with L/W ratio of 1.1-1.3:1. Rind color is medium green background with wide darker green stripes. This phenotype is known to those skilled in the art as "round-oval dark mottle stripe" watermelon fruit. Fruit of Line W-1488 is of round shape with L/W ratio of 1.0 to 1.1:1. Rind color is light green with some faint mottle/net pattern in the background. This phenotype is known to those skilled in the art as "round gray (or light green)" watermelon fruit. These four lines provide an array of phenotypic diversity amongst the cultivated types.

In the fall of 2000, the respective F1s were used as females to backcross to the above four inbreds, creating the backcross 1 (BC1) generation.

The BC1 generation plants were grown in the spring of 2001, and selections were made based on overall vigor. It was difficult to take the alleles from the PI line into the cultivated types because many of the BC1 and even BC2 plants died. Variation in vine vigor was observed that was associated with survivability. Vine vigor was assumed to be associated with general vigor, and perhaps with pathogen resistance.

The respective BC1 lines, derived from the original four inbreds were crossed as females as follows:

1. [[W-1128×PI296341]F1×W-1128](this is the W-1128 BC1)×W-1128
2. [[W-1119×PI296341]F1×W-1119](this is the W-1119 BC1)×W-1119
3. [[W-1488×PI296341]F1×W-1488](this is the W-1488 BC1)×W-1488
4. [[W-2388×PI296341]F1×W-2388](this is the W-2388 BC1)×W-2068
5. [[W-2388×PI296341]F1×W-2388](this is the W-2388 BC1)×BSI-2543
6. [[W-2388×PI296341]F1×W-2388](this is the W-2388 BC1)×BSI-2527

In these six crosses, the first three were recurrent parent backcrosses. Cross number four was to line W-2068, which is very similar to original parent W-2388. Crosses five and six were to new inbreds. The recurrent backcross program aims to add one or more new traits from the donor parent (in this case, PI296431), while retaining the phenotype of the recurrent parent. However, watermelon breeding is a dynamic process, so it is not uncommon to change the recurrent parent as newer inbred lines are being developed concurrently. Crosses four through six, therefore, were not technically creating the BC2 generation. For clarity in describing the generations, these crosses will be referred to as the BC2* generation. The BC2 and BC2* generation were grown in the summer of 2001. As with the BC1 generation, selection for vine vigor was made. Females thus selected were used to create the BC3 and BC3* generation.

1. W-1128 BC2×W-1128=BC3
2. W-1119 BC2×W-2741=BC3*
3. W-1488 BC2×W-1488=BC3
4. W-2068 BC2*×W-2068=BC3*

5. BSI-2543 BC2*×BSI-2543=BC3*
6. BSI-2527 BC2*×BSI-2527=BC3*

In the fall of 2001, the BC3 and BC3* lines were grown, and selection was again applied for vine vigor. Selected plants were then crossed to create the BC4 and BC4* generations, respectively.

7. W-1128 BC3×W-1128=BC4
8. W-2741 BC3*×W-2741=BC4*
9. W-1488 BC3×W-1488=BC4
10. W-2068 BC3*×W-2068=BC4*
11. BSI-2543 BC3*×BSI-2543=BC4*
12. BSI-2527 BC3*×BSI-2527=BC4*

In addition to selecting for vine vigor, examination of BC3 and BC3* fruit, which contained the BC4 and BC4* generation seed, produced an unexpected finding. Although the BC3 generation still performs poorly when evaluated by current horticultural characteristics, the fruits were examined for quality characteristics. Although most fruit had poor quality, breeder observations as to a small number of fruit included the following: "good fruit color, sweet taste and ultra firm flesh-like an apple." The unexpected finding was that both ultra firm flesh and sweet tasting flesh could be created. The possibility of creating a sweet tasting flesh, combined with ultra firm flesh for the cut fruit segment of the marketplace resulted in a bifurcation of breeding objectives. Applicants initiated a new project with the goal of creating ultra firm flesh watermelon fruits with sweet taste.

Example 2

Self-Pollinations of Plants Bearing Ultra Firm Flesh Fruit and Early Flesh Firmness Data In the spring of 2002, the BC4/BC4* generation was grown and evaluated qualitatively for sweet taste, fruit flesh firmness, and horticultural characteristics. Based on these evaluation criteria, plants were selected to create the next generation. Instead of creating another backcross generation, however, each selection from the lines being developed in parallel was self pollinated. The crossing produced the BC4S1/BC4*S1 generation.

In the summer of 2002, the BC4S1/BC4*S1 generation was grown and evaluated qualitatively for sweet taste, fruit flesh firmness, and horticultural characteristics. Based on these evaluation criteria, plants were selected to create the next generation. Self pollination of the selected plants created the BC4S2/BC4*S2 generation.

In the fall of 2002, the BC4S2/BC4S*2 generation was grown and evaluated qualitatively for sweet taste, fruit flesh firmness, and horticultural characteristics. Based on these evaluation criteria, plants were selected to create the next generation. Self pollination of the selected plants created the BC4S3/BC4S*3 generation.

In the spring of 2003 the BC4S3/BC4S*3 generation was grown and evaluated qualitatively for sweet taste, fruit flesh firmness, and horticultural characteristics. Based on these evaluation criteria, plants were selected to create the next generation. Self pollination of the selected plants created the BC4S4/BC4S*4 generation.

For the BC4S3 fruit, both qualitative and quantitative data were obtained for flesh firmness. Specifically, ninety three fruits from individual BC4S3 plants were evaluated for firmness with a penetrometer (model FT011 with an 8 millimeter probe, QA Supplies, Norfolk, Va.). The FT011 penetrometer has a gauge that reads PF, which is an improper abbreviation for pound force. Pound force is a British Engineering measurement scale for pressure, and is properly abbreviated lbf. The conversion from the British measurement system to the International System of Units (SI) is 1 lbf=4.448 newtons. For all flesh firmness measurements using a penetrometer, mature fruits were detached from the plant and cut in an equatorial direction. For orientation, fruits have a stem end and a blossom end. Equatorial slicing means that the fruits are halved such that each half has the blossom end or stem end the farthest distance from the cut site. Samples were taken from the center of the cut fruit. For diploid fruits, sampling occurred inside the seeded ring. Although triploid fruits have few to no seeds, sampling occurred within the same core area of the split fruit. Each half was sampled with the penetrometer, with a total of three to five readings per fruit. Firmness data are reported as an average of the three to five readings.

Even after several generations attempting to fix the firm flesh genotype combined with acceptable horticultural characteristics, including sweetness, FIG. 1 shows that significant fruit flesh firmness variation still existed in these samples. Although the data in FIG. 1 indicate significant variation, it was clear that improvements to fruit firmness had been made. The arrow shows the average firmness rating of the recurrent parents. Even at this early generation in product development, approximately 43% of the fruits have firmness measurements of not less than 4 lbf.

Some phenotypes are determined by the genotype at one locus. These simple traits, like those studied by Mendel, fall in discontinuous categories such as green or yellow seeds. Most variation observed in nature, however, is continuous, like yield in field corn, or human blood pressure. FIG. 1 shows a continuous-type pattern of firm flesh variation, similar to a normal distribution. Unlike simply inherited traits, continuous variation can be the result of polygenic inheritance. Loci that affect continuous variation are referred to as quantitative trait loci (or QTLs). Variation in the phenotype of a quantitative trait is the result of the allelic composition at the QTLs and an environmental effect. Applicants identified several potential causes for the variation: (1) the fruit firmness trait may be controlled by several to many QTLs; (2) the fruit firmness trait may be caused by one or a few genes, but have a low heritability; and (3) the trait may be both polygenic and have low heritability. Those skilled in the art recognize that the marketplace requires product uniformity. Thus, the utility of the invention is higher for those traits with high heritability that are not greatly affected by the environment. The heritability of a trait is the proportion of the phenotypic variation attributed to the genetic variance. This ratio varies between 0 and 1.0. Thus, a trait with heritability near 1.0 is not greatly affected by the environment. Because the fruit firmness variation shown in FIG. 1 did not explain the cause of the variation, further experiments were conducted, as described in the examples below, to determine the cause of the variation.

Example 3

Generation of Diploid Hybrids with Ultra Firm Flesh Trait

In the fall of 2002, in addition to the self pollinations, crosses with selected BC4S2/BC4S*2 generation plants were made to other commercial inbreds that do not contain the ultra firm flesh phenotype. These crosses were made to test to what extent the ultra firm flesh trait would be dominantly inherited in a hybrid combination. Those skilled in the art will recognize the importance of establishing how well traits developed in inbred lines function in a hybrid combination.

In the spring of 2003, these test hybrids were evaluated in Florida and California. Although many hybrid combinations were tested in these trials, most of these data are not shown. Instead, data from four top performing hybrids across two trialing locations are shown in Table 4 and Table 5. Hybrids were evaluated by a number of criteria, including the rind color pattern. For these hybrids, all had a mottled stripe pattern, designated MS. Also evaluated were fruit length and width, rind thickness, flesh color, firmness and sweetness levels.

When determining sweetness levels quantitatively, Applicants used a refractometer to measure brix levels. Specifically, brix levels were measured with a digital, hand-held refractometer (Leica Microsystems model AR200, Reichert Inc., Depew, N.Y.) according to manufacturer's instructions. Brix levels were determined after the penetrometer firmness readings, by squeezing a sampled fruit until drops of liquid fell into the well of the refractometer. One brix measurement was taken from each half of a cut fruit, and the data were recorded as an average.

Table 4 and Table 5 show that the test hybrids do exhibit small variation between the test sites. Taken together, however, the data show that these top performing hybrid combinations performed uniformly in the two locations. In particular, these hybrids consistently had ultra firm flesh, as measured by pound force of pressure and very good soluble solids, as measured by percentage brix.

Fruit flesh firmness data across the two locations provided insight into the genetics of the trait, answering questions as to heritability posed by the data shown in FIG. 1. First, these data show that the ultra firm flesh trait can be delivered into an F1 hybrid from a single parent. In other words, genetic loci selected in the method described herein affect fruit firmness in a dominant manner. This is a critical fact for the design of breeding strategies. Moreover, consistency in the firmness measurements across several hybrids in the two locations show that the ultra firm flesh alleles selected in the method described herein have a high heritability. Those skilled in the art recognize the importance of creating commercial lines with highly heritable horticultural traits. Specifically, such cultivars will allow growers to produce a crop with uniform market specifications.

TABLE 4

Test hybrid evaluations: Florida, Spring 2003

| Hybrid | Rind | Length (cm) | Width (cm) | Rind Thickness (cm) | Flesh Color | Firmness (lbf) | Sweetness (Brix) |
|---|---|---|---|---|---|---|---|
| 4201 | MS | 23 | 19.5 | 1.5 | Red | 8.0 | 9.7 |
| 4203 | MS | 25.5 | 21.5 | 1.5 | Red | 7.5 | 11.3 |
| 4204 | MS | 23 | 19 | 1.0 | Red | 6.0 | 9.3 |
| 4207 | MS | 25 | 20 | 2.0 | Red | 7.0 | 9.6 |

TABLE 5

Test hybrid evaluations: California, Spring 2003

| Hybrid | Rind | Length (cm) | Width (cm) | Rind Thickness (cm) | Flesh Color | Firmness (lbf) | Sweetness (Brix) |
|---|---|---|---|---|---|---|---|
| 4201 | MS | 22.5 | 17 | 1.5 | Red | 8.0 | 9.7 |
| 4203 | MS | 23 | 17 | 1.5 | Red | 8.0 | 10.3 |
| 4204 | MS | 25 | 18 | 2.0 | Red | 7.0 | 10.0 |
| 4207 | MS | 25 | 17 | 1.5 | Red | 6.0 | 10.3 |

FIG. 2 graphically displays the percent weight loss of these samples over a 16 day period. Multiple samples per line were tested; the triangles, circle and squares represent the mean values at each time point, and the sample standard deviations are shown as bars. Data in FIG. 2 show large differences in weight losses between the controls having softer fruit flesh and the fruits with the ultra firm flesh trait. The difference between the controls and the test hybrids with the ultra firm flesh phenotype was apparent by the first time point, which was approximately 6½ hours after the samples were cut. Therefore, although cut product from standard cultivars may have a shelf life of up to 2 to 3 days, product deterioration begins almost immediately after they are cut. These data show that the ultra firm flesh lines developed using the method described herein will resist the rapid liquid leakage now common in cut watermelon fruits. Because these ultra firm flesh fruits will retain liquid once cut, they will last longer in the minimally processed watermelon market.

Example 4

Final Self Pollinations and Creation and Evaluation of Triploid Hybrids

In the summer of 2003, the BC4S4/BC4S*4 generation, the generation of which is described above in Example 2, was grown and evaluated qualitatively for sweet taste, fruit flesh firmness, and horticultural characteristics. Based on these evaluation criteria, plants were selected to create the next generation. Self pollination created the BC4S5/BC4S*5 generation.

In the fall of 2003, the BC4S5/BC4S*5 generation was grown and evaluated qualitatively for sweet taste, fruit flesh firmness, and horticultural characteristics. Based on these evaluation criteria, plants were selected to create the next generation. Self pollination created the BC4S6/BC4S*6 generation.

In addition, quantitative firmness data were collected from the BC4S5 generation for lines that were qualitatively sweet. Specifically, twenty six lines were tested, and results are shown below in Table 6. Fourteen of these lines had a single fruit tested, and the remaining 12 lines had 2 or 3 fruits tested per line. The range of firmness amongst the twenty six lines ranged from a low of 4.0 lbf to a high of 8.0 lbf. For the lines that had multiple samples, 11 of the 12 lines showed no difference in the penetrometer measurements. One line did show a penetrometer measurement difference of 1 lbf. These data provide further insight as to questions raised by FIG. 1, which showed variation in the ultra firm flesh trait in the BC4S3 generation. In particular, it was unclear in the BC4S3 generation whether the ultra firm flesh trait displayed a low or high heritability. That many lines developed in parallel gave elevated, but different fruit firmness readings suggested that the ultra firm flesh is polygenic in nature. The very low intra-line variation shown in Table 6, together with the test hybrid data shown in Table 4 and Table 5 demonstrate that the ultra firm flesh trait has a high heritability. Those skilled in the art recognize the importance of creating commercial lines with highly heritable horticultural traits because such cultivars allow growers to produce a crop with uniform market specifications.

Table 6 shows the inbred line evaluations from the BC4S5/BC4S*5 generation.

TABLE 6

| Line-replication no. | Firmness |
|---|---|
| 3333 -1 | 7.0 lbf |
| 3333 -2 | 8.0 lbf |
| 3334 -1 | 5.0 lbf |
| 3334 -2 | 5.0 lbf |
| 3335 -1 | 8.0 lbf |
| 3335 -2 | 8.0 lbf |
| 3336 -1 | 5.0 lbf |
| 3336-2 | 5.0 lbf |
| 3337-1 | 5.0 lbf |
| 3339-1 | 4.0 lbf |
| 3340-1 | 4.5 lbf |
| 3340-2 | 4.5 lbf |
| 3340-3 | 4.5 lbf |
| 3341-1 | 5.0 lbf |
| 3346-1 | 5.0 lbf |
| 3346-2 | 5.0 lbf |
| 3347-1 | 6.0 lbf |
| 3347-2 | 6.0 lbf |
| 3347-3 | 6.0 lbf |
| 3348-1 | 6.0 lbf |
| 3348-2 | 6.0 lbf |
| 3348-3 | 6.0 lbf |
| 3349-1 | 5.0 lbf |
| 3350-1 | 5.0 lbf |
| 3350-2 | 5.0 lbf |
| 3350-3 | 5.0 lbf |
| 3352-1 | 5.5 lbf |
| 3353-1 | 6.0 lbf |
| 3355-1 | 8.0 lbf |
| 3355-2 | 8.0 lbf |
| 3357-1 | 5.0 lbf |
| 3357-2 | 5.0 lbf |
| 3358-1 | 5.0 lbf |
| 3358-2 | 5.0 lbf |
| 3359-1 | 6.0 lbf |
| 3378-1 | 7.0 lbf |
| 3380-1 | 7.0 lbf |
| 3384-1 | 7.0 lbf |
| 3386-1 | 7.0 lbf |
| 3387-1 | 8.0 lbf |
| 3388-1 | 7.0 lbf |
| 3390-1 | 6.0 lbf |
| 3390-2 | 6.0 lbf |
| 3392-1 | 8.0 lbf |
| 3392-2 | 8.0 lbf |
| 3394-1 | 5.5 lbf |
| 3394-2 | 5.5 lbf |
| 3396-1 | 7.0 lbf |
| 3396-2 | 7.0 lbf |
| 3397-1 | 7.0 lbf |
| 3397-2 | 7.0 lbf |
| 3398-1 | 7.5 lbf |
| 3399-1 | 7.5 lbf |
| 3399-2 | 7.5 lbf |
| 3400-1 | 7.5 lbf |
| 3401-1 | 7.5 lbf |
| 3401-2 | 7.5 lbf |
| 1577-1 | 8.0 lbf |
| 1577-2 | 8.0 lbf |
| 1577-3 | 8.0 lbf |
| 1577-4 | 8.0 lbf |
| 1577-5 | 8.0 lbf |
| 1577-6 | 8.0 lbf |
| 1577-7 | 8.0 lbf |

In addition to the self pollinations described above, crosses with selected BC4S4/BC4S*4 generation plants were made to other commercial tetraploid inbreds that do not contain the ultra firmness phenotype. These tetraploid× diploid crosses were made to test to what extent the ultra firm flesh trait would be dominantly inherited in a triploid hybrid combination. As shown in Table 7 below, the ultra firm flesh trait was inherited by the triploid seedless fruit.

TABLE 7

Mature fruit flesh firmness and sweetness scores. Firmness was measured as described herein with a penetrometer.

| Hybrid | Rind | Length (cm) | Width (cm) | Rind Thickness (cm) | Flesh Color | Firmness (lbf) | TSS (Brix) |
|---|---|---|---|---|---|---|---|
| SVR8034-7131 | TS | 28 | 24 | 1.2 | Red | 5.0 | 10.2 |
| SVR8034-7132 | MS | 26 | 25 | 1.0 | Red | 4.0 | 9.7 |
| 5VR8034-7133 | MS | 28 | 26 | 1.0 | Red | 5.0 | 10.5 |
| 5VR8034-7134 | MS | 26 | 24 | 1.1 | Red | 4.5 | 10.0 |

Example 5

Evaluation of Liquid-Retaining Flesh Characteristics of Ultra Firm Flesh Hybrids As described herein, studies agree that minimally processed products have a short shelf life of 2 to 3 days maximum (Perkins-Veazie et al. (1998) *Hortscience* 33:605; Wehner et al. in: Watermelons: Characteristics, Production and Marketing. Maynard, editor. ASHS Press, Alexandria, Va. (2001)). Although the maximum shelf life of cut watermelon fruit is only a few days, product quality begins to deteriorate rapidly after being processed. In cut products presented in plastic food containers, the consumer can see this rapid deterioration because liquid will leak out of the cut products and accumulate in the bottom of the container.

Mature fruits from the 2003 California hybrid trial (Example 3, Table 5) were evaluated for leakage using a liquid retention test as described herein (see FIG. 2). This test was performed at 4° centigrade. Fruits from test hybrids 4201, 4204 and 4207 were tested along with standard diploid and triploid hybrid controls. Test hybrids had the ultra firm flesh trait, with firmness readings of 8.0 lbf, 7.0 lbf and 6.0 lbf, respectively (Table 5). Controls had flesh firmness readings of <2.0 lbf and <2.5 lbf, respectively. To measure liquid loss, the edible portion of the fruits were cut into approximately 1" cubes and weighed. The approximate 1 inch cube size was chosen because this best approximates the processed product size found in retail outlets. Over a 16 day period, samples were re-weighed, and the liquid loss was estimated by calculating the percent weight loss.

Previous experiments have shown that although cut products from standard cultivars may have a shelf life of up to 2 to 3 days, deterioration as measured by water leakage begins almost immediately after cutting. In contrast, firm flesh lines resisted the rapid liquid leakage of the standard watermelon fruits. In certain embodiments of the invention, the cut flesh from the fruit of a watermelon of the invention with a genotype associated with an ultra-firm flesh phenotype loses less than about four percent water after three days storage at 4° centigrade. In certain embodiments of the invention, the cut flesh from the fruit of a watermelon of the invention with a genotype associated with an ultra-firm flesh phenotype loses less than about three percent or less than about two percent water after three days storage at 4° centigrade.

Watermelon fruit that retain liquid when cut will achieve a longer period of consumer acceptability after processing in the minimally processed watermelon market.

Example 6

Firm Flesh Watermelon

Firm flesh watermelon accessions have been identified in different species and varieties of the genus *Citrullus*, including *C. colocynthis*, *C. lanatus* var. *citroides*, and *C. lanatus* var. *lanatus*. PI296341 is a *C. lanatus* var. *citroides* accession originating from Africa available through the Germplasm Resources Information Network. PI296341 was backcrossed for several generations to all sweet type elite inbred lines (*C. lanatus* var. *lanatus*) to derive the ultra-firm flesh watermelon line 03LB3387-1.

A segregating population was developed from the cross of 03LB3387-1 and WAS-35-2438 by single seed descent for the mapping of the ultra-firm flesh trait. The population 03LB3387-1×WAS-35-2438 consisted of 186 F4:5 lines and was planted in three environments: Woodland, C A and Tifton, Ga. Test Year 1, and Woodland, Calif. in Test Year 3. The two experiments in Woodland, Calif., were planted in randomized complete block designs, while the Test Year 1 trial in Tifton was a complete randomized design. The parental lines 03LB3387-1 and WAS-35-2438 and their F1 hybrid were used as controls in each of the three trials. Firmness, total soluble solids (Brix), and lycopene data was collected in the Woodland and Tifton Test Year 1 trials. Firmness and Brix data was collected in Woodland in Test Year 3. Firmness data was collected as three penetrometer readings per fruit. The goal was to position readings longitudinally in the proximal, middle, and distal thirds of each fruit, and transversely mid-way between the rind and the center. Brix values were measured with a hand held refractometer (Atago, model PAL-1) using juice extracted with a citrus juicer from fruit samples (~11.5 cm$^3$) with mature-red color. Lycopene content was quantified by HPLC using a bulk of 4 to 5 core samples (~21 cm$^3$ each) taken from multiple flesh positions of fruit with mature-red color. Data was obtained in Test Year 1 using a penetrometer with a maximum reading of 12 lb/F; therefore, it is possible that for the Test Year 1 trials, a reported value of 12 may actually represent a value greater than 12 lb/F. During the Test Year 3 trial, data was obtained with an instrument that had a range of readings from 1 to 30 lb/F. Therefore, data for each of the three trials was analyzed separately instead of deriving phenotypic means and conducting QTL mapping analysis across the three environments.

Figure 4:
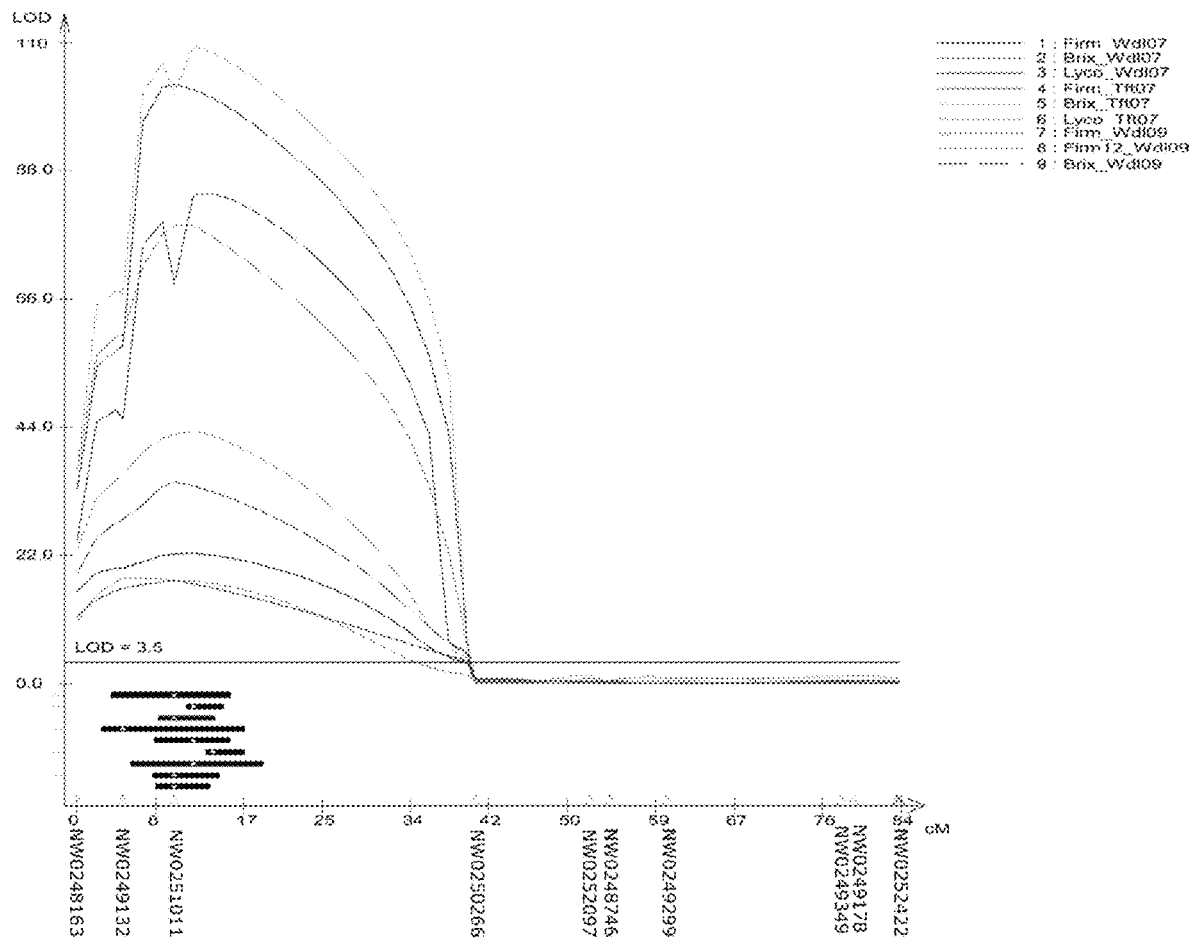
FIG. 4 shows the major firmness QTL identified on linkage group 9 (of the genetic map of the 03LB3378-1× WAS-35-2438 derived population) and co-localized QTL for Brix and lycopene content identified using QTL Cartographer. Black bars show the QTL curves correspond to the 2-LOD confidence intervals and white squares on each bar identify the QTL peaks.

Least square means for firmness, Brix, and lycopene content were generated for each family in each of three environments. Firmness phenotypes showed a bimodal distribution, implying that a single major QTL segregates for firmness in the mapping population (FIG. 4). The parental lines 03LB3387-1 and WAS-35-2438 and their F1 hybrid showed consistent phenotypes across locations and years (Table 8).

TABLE 8

Phenotypic means for firmness, Brix, and lycopene content of parental lines (03LB3387-1 and WAS-35-2438) and their F1 hybrid for each of the three trials.

| | Woodland Test Year 1 | | | Tifton Test Year 1 | | | Woodland Test Year 3 | |
|---|---|---|---|---|---|---|---|---|
| | Firmness | Brix | Lycopene | Firmness | Brix | Lycopene | Firmness | Brix |
| O3LB3387 | 10.98 | 9.00 | 49.68 | 10.59 | 8.85 | 44.70 | 11.67 | 9.04 |
| WAS-35-2438 | 2.11 | 10.18 | 61.33 | 2.43 | 11.68 | 67.00 | 2.15 | 10.64 |
| F1 | 7.59 | 9.87 | 62.26 | 8.08 | 10.88 | 79.24 | 6.10 | 10.29 |

One-hundred and eighty six 03LB3387-1×WAS-35-2438 lines were genotyped at the F4 generation using 1,536 SNP markers. A linkage map of the segregating population was constructed using 404 polymorphic markers with JoinMap software. The genetic map consisted of 19 linkage groups ranging in length from 4.5 to 142.1 cM, and had an average length of 64.1 cM. The average distance between adjacent SNP markers across the 19 linkage groups was 3.9 cM.

Figure 5:
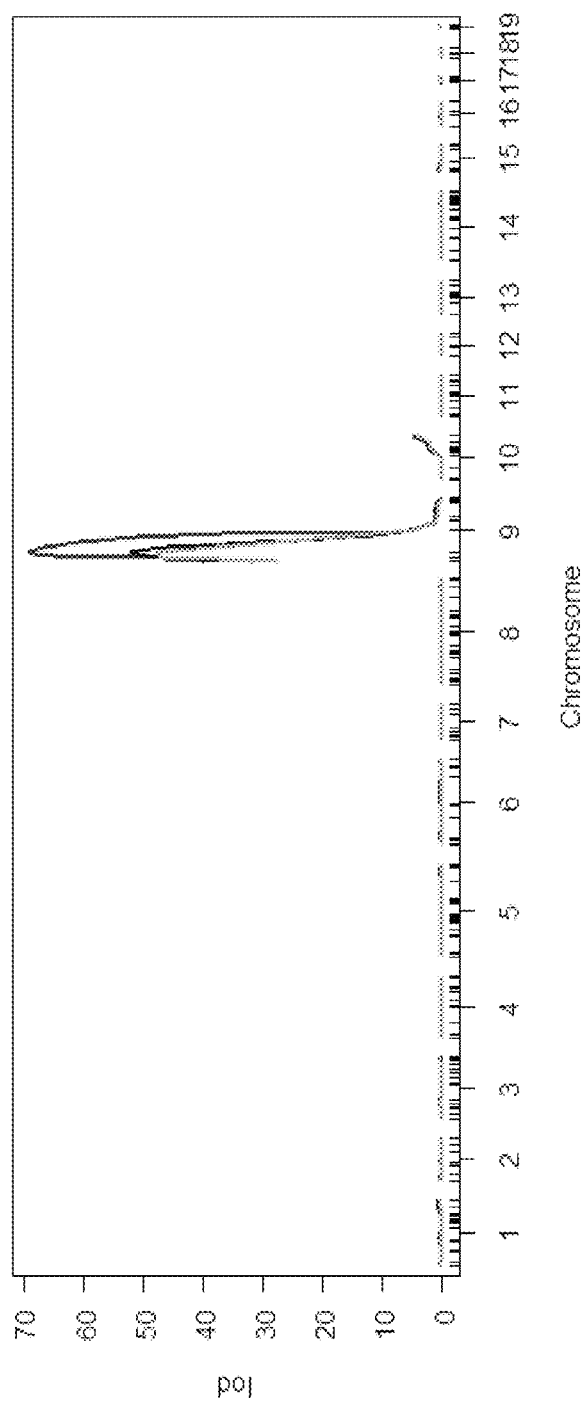
FIG. 5 presents a graph showing a major QTL for firmness identified on linkage group 9 using Rqtl. The graph presents an overlay of LOD curves of single-QTL genome scans conducted by three interval mapping methods (EM algorithm), Haley-Knott regression and multiple imputations for the 19 linkage groups of the 03LB3387×WAS-35-2438 genetic map.
Figure 6:
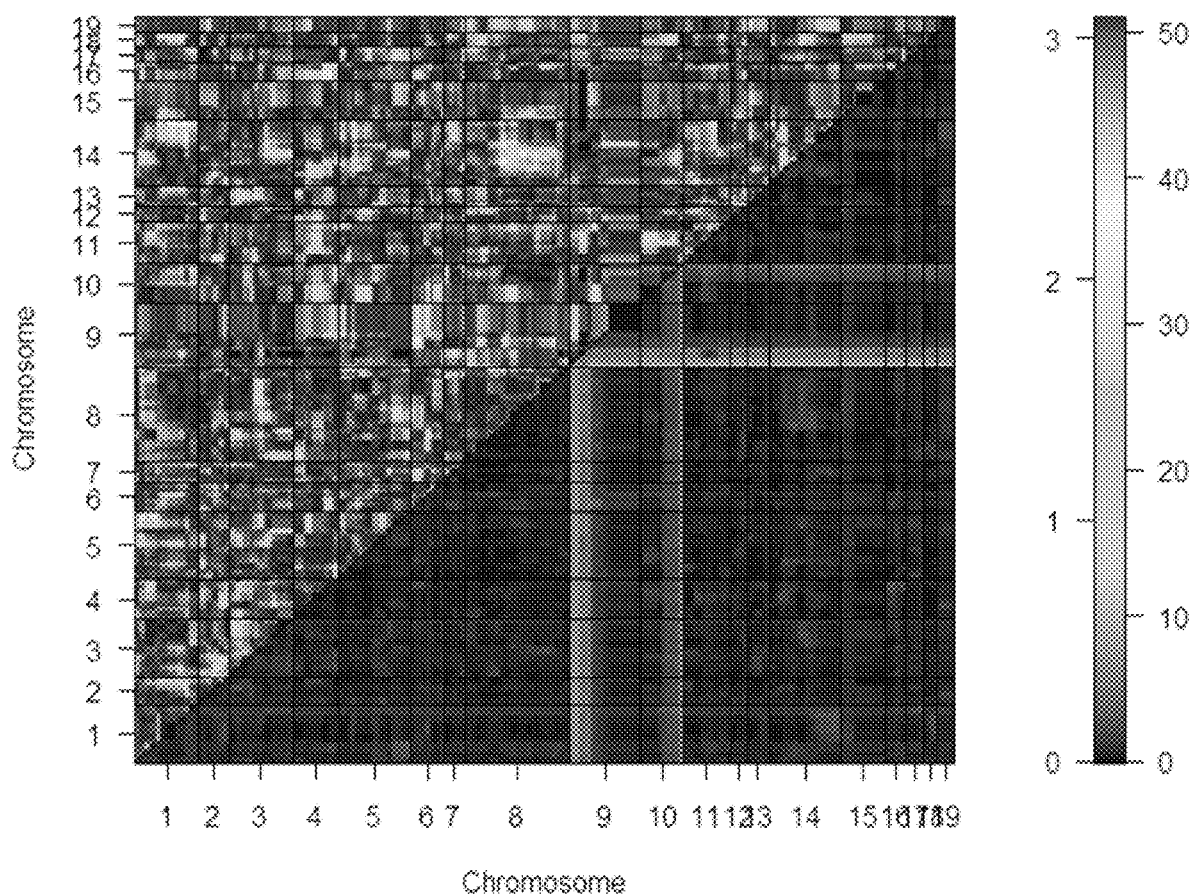
FIG. 6 presents a heat plot corresponding to two-QTL genome scans and shows the main effect for firmness identified on linkage group 9 below the diagonal and the lack of two-locus epistatic interactions above the diagonal.

QTL mapping analysis using composite interval mapping in QTL Cartographer identified a major locus controlling firmness on the proximal end of linkage group 9 (FIG. 5). QTL for Brix and lycopene content were also mapped in the same genomic interval and had moderate to low QTL effects (Table 9).

TABLE 9

QTL identifiers for firmness, Brix, and lycopene content on linkage group 9 of the genetic map of the 03LB3378-1 × WAS-35-2438 derived population. Position of the QTL on the linkage group (cM), additive and dominance effects of the QTL and 2-LOD confidence intervals are reported. (Woodland, CA Test Year 1 (Wdl1); Tifton, GA Test Year 1 (Tft1); Woodland, CA Test Year 3 (Wdl3)).

| Traits | cM | Additive effect | Dominance effect | 2-LOD left | 2-LOD right |
|---|---|---|---|---|---|
| Firmness_Wdl1 | 9.9 | 4.0051 | 0.4522 | 8.2 | 13.4 |
| Firmness_Tft1 | 13.9 | 3.6203 | 0.1133 | 13.4 | 16.9 |
| Firmness_Wdl3 | 9.9 | 5.2477 | −0.7243 | 8.5 | 13.9 |
| Brix_Wdl1 | 9.9 | −0.8533 | 0.0026 | 7.9 | 14.3 |
| Brix_Tft1 | 11.9 | −1.3193 | 0.1075 | 8.1 | 15.4 |
| Brix_Wdl3 | 9.9 | −0.6574 | 0.2705 | 3.7 | 15.5 |
| Lycopene_Wdl1 | 11.9 | −11.2121 | 0.9482 | 5.7 | 18.8 |
| Lycopene_Tft1 | 4.7 | −9.1304 | −20.594 | 2.7 | 16.9 |

The QTL were consistent across the three environments trialed and their 2-LOD intervals overlapped (FIG. 4; Table 9). Results were also confirmed with single- and two-QTL genome scans in Rqtl (FIG. 5) (The analysis presented in FIG. 5 uses phenotypic data of the Woodland Test Year 1 trial. Analysis was also conducted and had similar results using phenotypic data of Tifton Test Year 1 and Woodland Test Year 3 trials). The QTL for flesh firmness was localized to the genomic region flanked by NW0251464 (SEQ ID NO:

1) and NW0250266 (SEQ ID NO: 18), and the peak of the QTL was in close proximity to NW0251011 (SEQ ID NO: 12), NW0249132 (SEQ ID NO: 7), NW0248163 (SEQ ID NO: 9), and NW0250266 (SEQ ID NO: 18). Linkage group 9 from the genetic map of the 03LB3378-1×WAS-35-2438 population was later aligned to linkage group 2 of a consensus watermelon SNP map constructed with three additional segregating populations (Table 9). Additional markers were identified within the QTL interval including: NW0248953 (SEQ ID NO:2); NW0250301 (SEQ ID NO: 3), NW0248949 (SEQ ID NO: 4), NW0248646 (SEQ ID NO: 5), NW0249077 (SEQ ID NO: 6), NW0252494 (SEQ ID NO: 8), NW0252274 (SEQ ID NO: 10]), NW0248905 (SEQ ID NO: 11), NW0248869 (SEQ ID NO: 13), NW0251470 (SEQ ID NO: 14), NW0251308 (SEQ ID NO: 15), NW0250718 (SEQ ID NO: 16), and NW0248059 (SEQ ID NO: 17). The markers NW0252274 (SEQ ID NO: 10), NW0248646 (SEQ ID NO: 5), and NW0250301 (SEQ ID NO: 3) were found to predict the firm flesh phenotype accurately in diverse watermelon germplasm.

TABLE 10

Table 10. Sequences of certain polymorphic nucleic acid markers in proximity to a QTL locus associated with an ultra-firm flesh phenotype. Mature fruit flesh firmness and sweetness scores. Firmness was measured as described herein with a penetrometer.

| Marker Name | SEQ ID NO: | Polymorphic Position | Sequence |
|---|---|---|---|
| NW0251646 | 1 | 61 | gacaactgcaagagaantttttcaacatgaaacattcttcagcaaggaatgt tatcgagc[a/g]agcgtttgggttgctaaagcagcagtgggctattcttagt gaaacataattctatccaa |
| NW0248953 | 2 | 61 | ttgaaagttattcgtttactgaatgatgaggcgattggcatatcaaaagtctc ctttatt[a/t]gacgaggctaagagttgtggatatgatctggaagttgtctctt tctctcatattcgttat |
| NW0250301 | 3 | 61 | ggtggaactaagctcgacaacaatgagcatcaacctaccgagcgagaag gcactattgcg[a/g]ttagcaacatggaaaagtagtcctgatcttcgttctc gtgtagactatgtcttaggactt |
| NW0248949 | 4 | 61 | ggactccagccagaacatagacatcccccaccccatctgaaaaactaat attgtcccca[a/g]tgtgagaaagaaaanaagagcatgggacaaatga gaagggaaacaaagaacttccctga |
| NW0248646 | 5 | 61 | tcaacaataaccctagagaagaccttaacaaacacttgaaggattttcacat ctgaggac[a/c]tttccattctctttgaaggatggacaaatgattggttgtac tatcaacctcctggatcga |
| NW0249077 | 6 | 45 | tgcaggtatccttatgatctgaaatatcatcaagattacacttta[a/c]tcgctt gaataatcagaaatttcaaagtgtttatttacctgtaatcttcaaaaagaagca |
| NW0249132 | 7 | 61 | aggataaacaaattcacatacacttttcccaaatacatttaaaaggaaaattg gagaggg[t/c]caaataagtcaagaggctaagctgtaatgaatataacag ctttgttcaagttaaaccaat |
| NW0252494 | 8 | 61 | acaaaattctttccaaaaatgtaaaattctcaattatggaaagttggcgccgc gatgcta[t/c]tggctagagccgcggtgctgtgcgtcatgcaaacctacc ctcggcgctgtgccgcagcg |
| NW0248163 | 9 | 61 | gaaatttaggccacccacatgccttcttcgagtccttcagcattgggggttat cttgta[a/c]tcgagttacccacatgccttgtccgagtccttcaacattggg aaccatttctatatctcg |
| NW0252274 | 10 | 61 | cttctcggaaatacttcatctctatggacatcaccttccttgaggataaaccct tctttc[t/c]cgttagtcctcgtcagggagagagtagtagtgaagagactaa ctgttcatcaccttcaa |
| NW0248905 | 11 | 61 | ggtcacagattcaatctctaaagttgtatgccaccaaacttagaacctgcaa ttactacg[a/g]atttgacatccatataccacaaatgaatctacacgtttgttg ttttnaatgaactaaaaa |
| NW0251011 | 12 | 61 | atattcgagttggccaaataggtaacttattattttcttgagtttgttaacatgat aata[t/c]tactcaacgaaatcctatgatagctacacatttgagaatgcataa acaaactcgtattg |
| NW0248869 | 13 | 61 | aaaattttatgtacaggctgttacagttcgtcctttatctgctgtcagctccctc gtacg[t/g]tttgcagaggagccccagatgtttgccattgaattact |
| NW0251470 | 14 | 61 | gtttggaactgttatatccccntaaaactgctcaatgttatctcagagtgagctt ctacca[a/t]taaagctccttgttctggtnccaaaaaacacttccaccttccn attttnggtctctct |
| NW0251308 | 15 | 61 | caattgctgcagatgtaactgaaagaacaatcaangttctaggatggcatc attttgagt[t/c]tagtttcctaataaagtgttcatctgtgttttngatgtgctaa atcagtggaggcnttt |

TABLE 10-continued

Table 10. Sequences of certain polymorphic nucleic acid markers in proximity to a QTL locus associated with an ultra-firm flesh phenotype. Mature fruit flesh firmness and sweetness scores. Firmness was measured as described herein with a penetrometer.

| Marker Name | SEQ ID NO: | Polymorphic Position | Sequence |
|---|---|---|---|
| NW0250718 | 16 | 61 | tgacggcggttgctgcattgctcatggctgtatggttcatgtctacgattgga tgctcga[t/c]gaacaccctccgatcaatctcgattatcagcgagtcaacg atgttgggtggatcgatgct |
| NW0248059 | 17 | 61 | acttaattgaatctaatagatgaagttcaattacgcaagtacaaaaanttact agttaat[a/g]tgtcatacacgcaagtcaaagatctttatgcatggtgcctc caatttgttatcagagacc |
| NW0250266 | 18 | 61 | gtatcttttgtgtccgtattagcttgcgacctcttcgagtggttatagttaggtt gtacg[t/c]tttgatgtttttctatgttggtatgagtggcttggggattcttttcg gagcattcatgtt |

Polymorphic nucleotide bases are designated in the Sequence Listing provided herewith according to the WIPO Standard ST.25 (1998), Table 1, as follows: r=g or a (purine); y=t/u or c (pyrimidine); m=a or c; (amino); k=g or t/u (keto); s=g or c (strong interactions 3H-bonds); w=a or t/u (weak interactions 2H-bonds); b=g or c or t/u (not a); d=a or g or t/u (not c); h=a or c or t/u (not g); v=a or g or c (not t, not u); and n=a or g or c or t/u (unknown, or other; any.) Deletions are also indicated as provided in Table 3.

All references cited herein are hereby expressly incorporated herein by reference.

DEPOSIT INFORMATION

A deposit of the *Seminis* Vegetable Seeds proprietary inbred and hybrid watermelon line 3347 disclosed above and recited in the appended claims has been made with NCIMB Ltd, 23 St. Machar Drive, Aberdeen AB24 3RY. The date of the deposit was 1 Jul. 2004. The deposit of 2500 seeds for this variety were taken from the same deposit maintained by *Seminis* Vegetable Seeds since prior to the filing date of this application. Upon issuance of a patent, all restrictions upon the deposit will be removed, and the deposit is intended to meet all of the requirements of 37 C.F.R. § 1.801-1.809. The NCIMB accession numbers for inbred line 3347 was deposited as Accession No. NCIMB 41230.

Although the foregoing invention has been described in some detail by way of illustration and example for purposes of clarity and understanding, it will be obvious that certain changes and modifications may be practiced within the scope of the invention, as limited only by the scope of the appended claims.

The invention claimed is:

1. An elite watermelon plant, or a part thereof, comprising an ultra-firm watermelon flesh allele of at least one loci selected from the group consisting of SEQ ID NOs: 3, 5, and 10; wherein said ultra-firm watermelon flesh allele is introgressed from PI296341, and wherein a fruit of said elite watermelon plant has flesh that resists a pressure of at least 3.5 pound/force (lb/F) and has soluble solids of at least 6 brix;

wherein said ultra-firm watermelon flesh allele of NW0250301 is a G nucleotide at position 61 of SEQ ID NO:3, said ultra-firm watermelon flesh allele of NW0248646 is a C nucleotide at position 61 of SEQ ID NO:5, or said ultra-firm watermelon flesh allele of NW0252274 is a C nucleotide at position 61 of SEQ ID NO:10.

2. The elite watermelon plant, or a part thereof, of claim 1, wherein a fruit of said watermelon plant comprises edible parts having not less than 8 Brix.

3. The elite watermelon plant, or a part thereof, of claim 1, wherein a fruit of said watermelon plant comprises edible parts having not less than 10 Brix.

4. The elite watermelon plant, or a part thereof, of claim 1, wherein said part is selected from the group consisting of pollen, an ovule, a leaf, an embryo, a root, a root tip, an anther, a flower, a fruit, a stem, a shoot, a seed, a protoplast, a cell, and a callus.

5. The elite watermelon plant, or a part thereof, of claim 1, wherein cut flesh from a fruit of said watermelon plant loses less than three percent water after three days storage at 4° Celsius.

6. The elite watermelon plant, or a part thereof, of claim 1, wherein said plant is diploid.

7. The elite watermelon plant, or a part thereof, of claim 1, wherein said plant is triploid.

8. The elite watermelon plant, or a part thereof, of claim 1, wherein said plant is tetraploid.

9. The elite watermelon plant, or a part thereof, of claim 1, wherein said plant is a hybrid.

10. The elite watermelon plant, or a part thereof, of claim 1, wherein said plant is seedless.

11. A watermelon plant, or a part thereof, comprising an ultra-firm watermelon flesh allele of at least one loci obtainable from PI296341 and selected from the group consisting of NW0250301 (SEQ ID NO: 3), NW0248646 (SEQ ID NO:5), and NW0252274 (SEQ ID NO:10); wherein a mature fruit of said watermelon plant has flesh that resists pressure of at least 3.5 lb/F and has soluble solids of at least 6 brix;

wherein said ultra-firm watermelon flesh allele of NW0250301 is a G nucleotide at position 61 of SEQ ID NO:3, said ultra-firm watermelon flesh allele of NW0248646 is a C nucleotide at position 61 of SEQ ID NO:5, or said ultra-firm watermelon flesh allele of NW0252274 is a C nucleotide at position 61 of SEQ ID NO:10.

12. The watermelon plant of claim 11, wherein a fruit of said watermelon plant has flesh that resists a pressure of at least 4 lb/F.

13. The watermelon plant of claim 11, wherein cut flesh from a fruit of said watermelon plant loses less than three percent water after three days storage at 4° Celsius.

14. A part of the watermelon plant of claim 11, wherein said part is selected from the group consisting of pollen, an ovule, a leaf, an embryo, a root, a root tip, an anther, a flower, a fruit, a stem, a shoot, a seed, a protoplast, a cell, and a callus.

15. An elite watermelon plant, or a part thereof, comprising an ultra-firm watermelon flesh allele obtainable from PI296341 of at least one loci selected from the group consisting of SEQ ID NOs: 3, 5, and 10; wherein a mature fruit of said elite watermelon plant has flesh that resists pressure of at least 3.5 lb/F and has soluble solids of at least 6 brix;

wherein said ultra-firm watermelon flesh allele of NW0250301 is a G nucleotide at position 61 of SEQ ID NO:3, said ultra-firm watermelon flesh allele of NW0248646 is a C nucleotide at position 61 of SEQ ID NO:5, or said ultra-firm watermelon flesh allele of NW0252274 is a C nucleotide at position 61 of SEQ ID NO:10.

16. The elite watermelon plant, or a part thereof, of claim 15, wherein said plant comprises an ultra-firm flesh allele at one or more loci selected from the group consisting of SEQ ID NOs: 3, 5, and 10.

17. The elite watermelon plant, or a part thereof, of claim 15, wherein said plant comprises an ultra-firm flesh allele at two or more loci selected from the group consisting of SEQ ID NOs: 3, 5, and 10.

18. The elite watermelon plant, or a part thereof, of claim 15, wherein said plant comprises ultra-firm flesh alleles at—SEQ ID NOs: 3, 5, and 10.

19. The elite watermelon plant, or a part thereof, of claim 15, wherein said ultra-firm watermelon flesh allele is from PI296341.

20. The elite watermelon plant, or a part thereof, of claim 15, wherein a fruit of said watermelon plant comprises edible parts having not less than 8 Brix.

21. The elite watermelon plant, or a part thereof, of claim 15, wherein a fruit of said watermelon plant comprises edible parts having not less than 10 Brix.

22. The elite watermelon plant, or a part thereof, of claim 15, wherein said part is selected from the group consisting of pollen, an ovule, a leaf, an embryo, a root, a root tip, an anther, a flower, a fruit, a stem, a shoot, a seed, a protoplast, a cell, and a callus.

23. The elite watermelon plant, or a part thereof, of claim 15, wherein a fruit of said watermelon plant has flesh that resists a pressure of at least about 4 lb/F.

24. The elite watermelon plant, or a part thereof, of claim 15, wherein cut flesh from a fruit of said watermelon plant loses less than about three percent water after three days storage at 4° Celsius.

25. The elite watermelon plant, or a part thereof, of claim 15, wherein said plant is diploid or tetraploid.

26. The elite watermelon plant, or a part thereof, of claim 15, wherein said plant is triploid.

27. The elite watermelon plant, or a part thereof, of claim 15, wherein said plant is a hybrid.

28. The elite watermelon plant, or a part thereof, of claim 15, wherein said plant is seedless.

29. The watermelon plant of claim 11, wherein a fruit of said watermelon plant comprises edible parts having not less than 8 Brix.

30. The watermelon plant of claim 11, wherein said plant is triploid.

31. The watermelon plant of claim 11, wherein said ultra-firm watermelon flesh allele is from PI296341.

32. The elite watermelon plant, or a part thereof, of claim 1, wherein said part is a seed.

33. The watermelon plant, or a part thereof, of claim 11, wherein said part is a seed.

34. The elite watermelon plant, or a part thereof, of claim 15, wherein said part is a seed.

* * * * *